(12) United States Patent
Schmidt-Dannert et al.

(10) Patent No.: US 9,909,143 B2
(45) Date of Patent: Mar. 6, 2018

(54) ENGINEERED SUBCELLULAR COMPARTMENTS

(71) Applicant: REGENTS OF THE UNIVERSITY OF MINNESOTA, Minneapolis, MN (US)

(72) Inventors: Claudia Margarete Schmidt-Dannert, Shoreview, MN (US); Swati Choudhary Saurkar, St. Louis Park, MN (US); Maureen Blacker Quin, Saint Paul, MN (US); Mark Anton Held, Saint Paul, MN (US)

(73) Assignee: REGENTS OF THE UNIVERSITY OF MINNESOTA, Minneapolis, MN (US)

( * ) Notice: Subject to any disclaimer, the term of this patent is extended or adjusted under 35 U.S.C. 154(b) by 304 days.

(21) Appl. No.: 14/354,183

(22) PCT Filed: Oct. 25, 2012

(86) PCT No.: PCT/US2012/061886
§ 371 (c)(1),
(2) Date: Apr. 25, 2014

(87) PCT Pub. No.: WO2013/063246
PCT Pub. Date: May 2, 2013

(65) Prior Publication Data
US 2014/0295520 A1    Oct. 2, 2014

Related U.S. Application Data

(60) Provisional application No. 61/551,264, filed on Oct. 25, 2011.

(51) Int. Cl.
*C12P 1/04*     (2006.01)
*C07K 14/255*   (2006.01)
*A62D 3/02*     (2007.01)

(52) U.S. Cl.
CPC .................. *C12P 1/04* (2013.01); *A62D 3/02* (2013.01); *C07K 14/255* (2013.01); *Y02P 20/582* (2015.11)

(58) Field of Classification Search
CPC .......................... C07K 14/125; C07K 2319/01
See application file for complete search history.

(56) References Cited

FOREIGN PATENT DOCUMENTS

WO    2011/017458 A1    2/2011
WO    2011/094765 A2    8/2011

OTHER PUBLICATIONS

Drubin, 1989; The yeast *Saccharomyces cerevisiae* as a model organisms for the cytoskeleton and cell biology. Cell Motility and Cytoskeleton 14:42-49.*

Yates et al. 2005; Proteomics of organelles and large cellular structures. Nature 6: 702-714.*
Bertin et al., "Enterohaemorrhagic *Escherichia coli* gains a competitive advantage by using ethanolamine as a nitrogen source in the bovine intestinal content," *Environ. Microbiol.*, Feb. 2011; 13(2):365-377.
Bloch et al., "Engineering a Novel Biosynthetic Pathway for Rosmarinic Acid in *E. coli.*," The Biotechnology Institute, Abstract and Poster.
Bobik et al., "The propanediol utilization (pdu) operon of *Salmonella enterica* serovar Typhimurium LT2 includes genes necessary for formation of polyhedral organelles involved in coenzyme $B_{12}$-dependent 1,2-propanediol degradation," *J. Bacteriol.*, Oct. 1999; 181(19):5967-5975.
Bonacci et al., "Modularity of a carbon-fixing protein organelle," *PNAS USA*, Jan. 10, 2012; 109(2):478-483.
Brinsmade et al., "Minimal functions and physiological conditions required for growth of *Salmonella enterica* on ethanolamine in the absence of the metabolosome," *J. Bacteriol.*, Dec. 2005; 187(23):8039-8046.
Buan et al., "The eutT gene of *Salmonella enterica* encodes an oxygen-labile, metal-containing ATP: corrinoid adenosyltransferase enzyme," *J Bacteriol.*, Sep. 2004; 186(17):5708-5714.
Burbulis et al., "Interactions among enzymes of the *Arabidopsis* flavonoid biosynthetic pathway," *PNAS USA*, Oct. 26, 1999; 96(22):12929-12934.
Cheng et al., "Bacterial microcompartments: their properties and paradoxes," *Bioessays*, Nov.-Dec. 2008; 30(11-12):1084-1095.
Cheng et al., "Genetic analysis of the protein shell of the microcompartments involved in coenzyme $B_{12}$-dependent 1,2-propanediol degradation by *Salmonella*," *J. Bacteriol.*, Mar. 15, 2011; 193(6):1385-1392.
Choudhary et al., "In vivo nano-bioreactors for biosynthesis and biocatalysis," poster and abstract; SIM Annual Meeting and Exhibition, New Orleans, LA; Jun. 24, 2011.
Choudhary et al., "Engineered Protein Nano-Compartments for Targeted Enzyme Localization," *PLoS ONE*, Mar. 12, 2012; 7(3).
Crowley et al., "Structure of the PduU shell protein from the Pdu microcompartment of *Salmonella*," *Structure*, Sep. 10, 2008; 16(9):1324-1332.
Dueber et al., "Synthetic protein scaffolds provide modular control over metabolic flux," *Nat. Biotechnol.*, Aug. 2009; 27(8):753-759.
Dunwell et al., "Cupins: the most functionally diverse protein superfamily?" *Phytochemistry*, Jan. 2004; 65(1):7-17.
Fan et al., "Short N-terminal sequences package proteins into bacterial microcompartments," *PNAS USA*, Apr. 20, 2010; 107(16):7509-7514.
Fontes, "Cellulosomes: highly efficient nanomachines designed to deconstruct plant cell wall complex carbohydrates," *Annu. Rev. Biochem.*, Jul. 2010; 79:655-681.
Goering et al., "Engineering of In Vivo Nanobioreactors," poster and presentation; iGEM Jamboree, Nov. 6-8, 2010; Massachusetts Institute of Technology, Cambridge, MA; 30 pgs.
Havemann et al., "Protein content of polyhedral organelles involved in coenzyme $B_{12}$-dependent degradation of 1,2-propanediol in *Salmonella enterica* Serovar Typhimurium LT2," *J. Bacteriol.*, Sep. 2003; 185(17):5086-5095.

(Continued)

*Primary Examiner* — Karen Cochrane Carlson
(74) *Attorney, Agent, or Firm* — Mueting, Raasch & Gebhardt, P.A.

(57) ABSTRACT

This disclosure describes a cell that includes an engineered subcellular compartment that generally includes a proteinaceous shell that includes at least one bacterial microcompartment (BMC) polypeptide. In some embodiments, the engineered subcellular compartment can further include one or more targeted enzymes. We further describe methods of making and using such cells.

26 Claims, 18 Drawing Sheets

(56) References Cited

OTHER PUBLICATIONS

International Search Report and Written Opinion dated Jan. 23, 2013, for International Application No. PCT/US2012/061886, filed Oct. 25, 2012; 14 pages.
Keasling, "Synthetic biology for synthetic chemistry," *ACS Chem Biol*, Jan. 18, 2008; 3(1):64-76.
Kerfeld et al., "Bacterial Microcompartments," *Annu. Rev. Microbiol.*, Oct. 2010; 64:391-408.
Kofoid et al., "The 17-gene ethanolamine (eut) operon of *Salmonella typhimurium* encodes five homologues of carboxysome shell proteins," *J. Bacteriol.*, Sep. 1999; 181(17):5317-5329.
Kovach et al., "pBBR1MCS: a broad-host-range cloning vector," *Biotechniques*, May 1, 1994; 16:800-802.
Lin et al, "Biosynthesis of caffeic acid in *Escherichia coli* using its endogenous hydroxylase complex," *Microb Cell Fact*, Apr. 4, 2012; 11:42.
Lopez-Gallego et al., "Multi-enzymatic synthesis," *Curr. Opin. Chem, Biol.*, Apr. 2010; 14(2):174-183. Available online Dec. 24, 2009.
Marasco et al., "Identification of carotenoid cleavage dioxygenases from *Nostoc* sp. PCC 7120 with different cleavage activities," *J. Biol. Chem.*, Oct. 20, 2006; 281(42):31583-31593.
Mauriello et al., "Bacterial mobility complexes require the actin-like protein, MreB and the Ras homologue, Mg1A," *EMBO*, Jan. 20, 2010; 29(2):315-326.
Menon et al., "*Halothiobacillus neapolitanus* carboxysomes sequester heterologous and chimeric RubisCO species," *PLoS One*, Oct. 30, 2008; 3:e3570.
Mori et al., "Identification of a reactivating factor for adenosylcobalamin-dependent ethanolamine ammonia lyase," *J Bacteriol.*, Oct. 2004; 186(20):6845-6854.
Muñoz et al., "Microwave-assisted immunostaining: a new approach yields fast and consistent results," *J. Neurosci. Methods*, 2004; 137:133-139.
Papapostolou et al., "Engineering and exploiting protein assemblies in synthetic biology," *Mol. Biosyst.*, Jul. 2009; 5(7):723-732.
Parsons et al., "Biochemical and Structural Insights into Bacterial Organelle Form and Biogenesis," *J. Biol. Chem.*, May 23, 2008; 283(21):14366-14375.
Parsons et al., "Synthesis of Empty Bacterial Microcompartments, Directed Organelle Protein Incorporation, and Evidence of Filament-Associated Organelle Movement," *Mol. Cell.*, Apr. 23, 2010; 38(2):305-315.
Penrod et al., "A pH-sensitive function and phenotype: evidence that EutH facilitates diffusion of uncharged ethanolamine in *Salmonella enterica*," *J Bacteriol.*, Oct. 2004: 186(20):6885-6890.
Penrod et al., "Conserving a volatile metabolic: a role for carboxysome-like organelles in *Salmonella enterica*," *J. Bacteriol.*, Apr. 15, 2006; 188(8):2865-2874.
Price et al., "Advances in understanding the cyanobacterial $CO_2$-concentrating-mechanism (CCM): functional components, Ci transporters, diversity, genetic regulation and prospects for engineering into plants," *J. Exp. Bot.*, May 7, 2008; 59(7):1441-1461.
Purnick et al., "The second wave of synthetic biology: from modules to systems," *Nat. Rev. Mol. Cell Biol.*, Jun. 2009; 10(6):410-422.
Rath et al., "Detergent binding explains anomalous SDS-PAGE migration of membrane proteins," *PNAS USA*, Feb. 10, 2009; 106(60):1760-1765.
Roof et al., "Autogenous regulation of ethanolamine utilization by a transcriptional activator of the eut operon in *Salmonella typhimurium*," *J. Bacteriol.*, Oct. 1992; 174(20):6634-6643.
Sambrook et al., *Molecular Cloning: A Laboratory Manual*, Cold Spring Harbor Lab Press, Cold Spring Harbor, NY; 1989.
Savage et al., "Spatially ordered dynamics of the bacterial carbon fixation machinery," *Science*, Mar. 5, 2010; 327(5970):1258-1261.
Schmidt-Dannert et al., "Molecular breeding of carotenoid biosynthetic pathways," *Nat. Biotechnol.*, Jul. 2000; 18(7):750-753.
Sheppard et al., "A rationale for autoinduction of a transcriptional activator: ethanolamine ammonia-lyase (EutBC) and the operon activator (EutR) compete for adenosyl-cobalamin in *Salmonella typhimurium*," *J. Bacteriol.*, Mar. 1994; 176(5):1287-1296.
Shetty et al., "Engineering BioBrick vectors from BioBrick parts," *J. Biol. Eng.*, Apr. 14, 2008; 2:5.
Shively et al., "Sequence homologs of the carboxysomal polypeptide CsoS1 of the thiobacilli are present in cyanobacteria and enteric bacteria that form carboxysomes—polyhedral bodies," *Can. J. Bot.*, Jun. 1998; 76(6):906-916.
Sriramulu et al., "*Lactobacillus reuteri* DSM 20016 produces cobalamin-dependent diol dehydratase in metabolosomes and metabolizes 1,2-propanediol by disproportionation," *J. Bacteriol.*, Jul. 1, 2008; 190(13):4559-4567.
Starai et al., "Acetate excretion during growth of *Salmonella enterica* on ethanolamine requires phosphotransacetylase (EutD) activity, and acetate recapture requires acetyl-CoA synthetase (Acs) and phosphotransacetylase (Pta) activities," *Microbiology*, Nov. 1, 2005; 151(11):3793-3801.
Steinmann et al., "In vivo enzyme immobilization by inclusion body display," *Appl. Environ. Microbiol.*, Aug. 2010; 76(16):5563-5569.
Stojiljkovic et al., "Ethanolamine utilization in *Salmonella typhimurium*: nucleotide sequence, protein expression, and mutational analysis of the cchA cchB eutE eutJ eutG eutH gene cluster," *J. Bacteriol.*, Mar. 1995; 177(5):1357-1366.
Takenoya et al., "Crystallographic insights into the pore structures and mechanisms of the EutL and EutM shell proteins of the ethanolamine-utilizing microcompartment of *Escherichia coli*," *J. Bacteriol.*, Nov. 15, 2010; 192(22):6056-6063.
Tanaka et al., "Atomic-level models of the bacterial carboxysome shell," *Science*, Feb. 22, 2008; 319:1083-1086.
Tanaka et al., "Structure and Mechanisms of a Protein-Based Organelle in *Escherichia coli*," *Science*, Jan. 1, 2010; 327:81-84.
Tsai et al., "Bacterial Microcompartments: Insights into the Structure, Mechanism, and Engineering Applications," *Progress in Molecular Biology and Translational Science*, Elsevier, Jan. 1, 2011; 103:1-20.
Urano et al., "Genetic analysis around aminoalcohol dehydrogenase gene of *Rhodococcus erythropolis* MAK154: a putative GntR transcription factor in transcriptional regulation," *Appl. Microbiol. Biotechnol.*, 2011; 89(3):739-746. Available online Oct. 16, 2010.
Vick et al., "Optimized compatible set of BioBrick™ vectors for metabolic pathway engineering," *Appl Microbiol Biotechnol*, Dec. 2011; 92:1275-1286. Available online Oct. 28, 2011.
Vogel et al., "Acetylornithinase of *Escherichia coli*: partial purification and some properties," *J. Biol. Chem.*, Jan. 1, 1956; 218(1):97-106.
Webster, "Microwave-assisted processing and embedding for transmission electron microscopy," *Methods Mol. Biol.*, Humana Press Inc., Totowa, NJ, 2007; 369:47-65.
Worsdorfer et al., "Directed evolution of a protein container," *Science*, Feb. 4, 2011; 331:589-592.
Yeates et al., "Protein-based organelles in bacteria: carboxysomes and related microcompartments," *Nat. Rev. Microbiol.*, Sep. 2008; 6(9):681-691.
Yeates et al., "Bacterial microcompartment organelles: protein shell structure and evolution," *Annu. Rev. Biophys.*, Apr. 2010; 39:185-205.
Yeates et al., "The protein shells of bacterial microcompartment organelles," *Curr. Opin. Struct. Biol.*, Apr. 2011:21(2):223-231.

* cited by examiner

S. enterica Eut BMCs

E. coli EutSMNLK BMCs

E. coli EutS BMCs

ENGINEERED SUBCELLULAR COMPARTMENTS

CROSS-REFERENCE TO RELATED APPLICATION

This application is a U.S. National Stage Application of International Application No. PCT/US2012/061886, filed Oct. 25, 2012, which was published on May 2, 2013, as International Patent Publication WO 2013/063246 A1, which claims priority to U.S. Provisional Patent Application Ser. No. 61/551,264, filed Oct. 25, 2011, each of which is incorporated herein by reference in its entirety.

GOVERNMENT FUNDING

The present invention was made with government support under Grant No. N00014-10-1-0157, awarded by the Office of Naval Research. The Government has certain rights in this invention.

SUMMARY OF THE INVENTION

In one aspect, this disclosure describes a cell that includes a non-native compartment comprising a proteinaceous shell comprising at least one bacterial microcompartment (BMC) polypeptide. In some embodiments, the non-native compartment can further include one or more targeted enzymes. In some of these embodiments, a targeted enzyme can include a compartment-specific targeting signal sequence.

In some embodiments, a BMC polypeptides can include a Eut polypeptide. In some embodiments, a Eut polypeptide can include a EutS polypeptide. In some cases, the proteinaceous shell can include a plurality of different BMC polypeptides. In some of these embodiments, the plurality of different BMC polypeptides can include BMC polypeptides from different bacterial species.

In some embodiments, at least one BMC polypeptide can include an affinity tag.

In some embodiments, the cell can include a plurality of compartments.

In another aspect, this disclosure describes a method that generally includes introducing into a host cell a polynucleotide that encodes at least one BMC polypeptide, thereby producing a transformed cell; and growing the transformed cell under conditions effective for the transformed cell to express the polynucleotide that encodes at least one BMC polypeptide and produce a non-native compartment that includes a proteinaceous shell that includes the at least one BMC polypeptide.

In some embodiments, the host cell can be a bacterium. In other embodiments, the host cell may be a yeast. In still other embodiments, the host cell may be an alga.

In yet another aspect, this disclosure describes a method that generally includes providing a cell that includes a non-native compartment that includes (a) a proteinaceous shell that includes at least one bacterial microcompartment (BMC) polypeptide, and (b) at least one enzyme that catalyzes conversion of a substrate to a product, and growing the cell under conditions effective for the at least one enzyme to catalyze conversion of the substrate to a product.

In some embodiments, the product can include a bioactive product. In other embodiments, the product can include a drug or a drug precursor. In other embodiments, the product can include a biofuel or a precursor of biofuel production. In still other embodiments, the enzyme can catalyzes a step in degrading or detoxifying a toxic substrate.

In some of these embodiments, the method can further include isolating at least a portion of the non-native compartments. In some of these embodiments, the non-native compartments may be isolated by contacting the non-native compartments with an affinity substrate having selective affinity for an affinity tag incorporated into the non-native compartment.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

DETAILED DESCRIPTION OF ILLUSTRATIVE EMBODIMENTS

Figure 1:
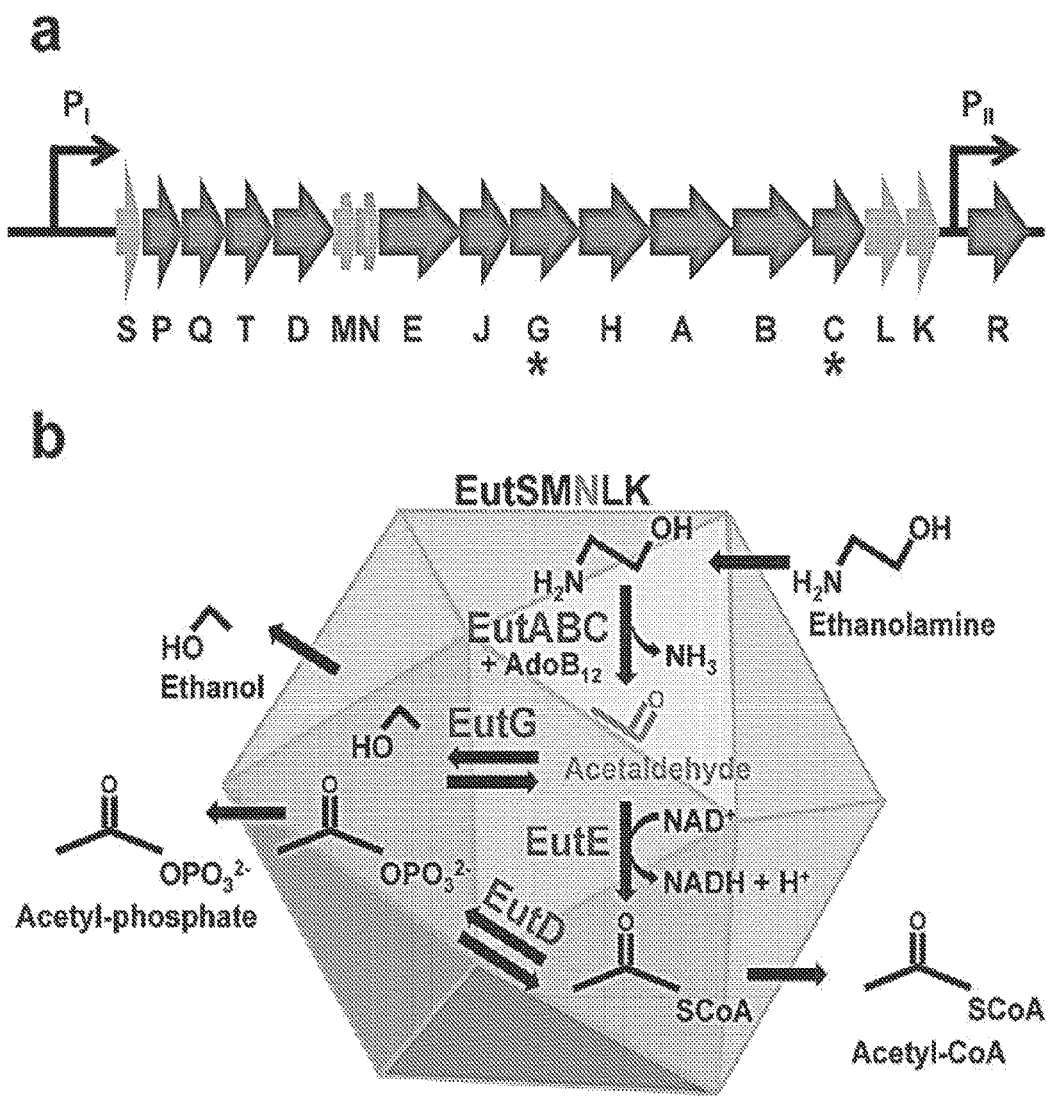
FIG. 1. Coenzyme-$B_{12}$-dependent ethanolamine utilization (eut) genes of *Salmonella enterica*. (a) eut operon in *S. enterica*. eutS, eutM, eutN, eutL and eutK encode BMC shell proteins that are proposed to form the Eut microcompartment (Kofoid et al. 1999 J Bacteriol 181:5317-5329). Asterisks indicate genes that encode for enzymes with predicted N-terminal signal sequences that target them to the BMC interior (Fan et al. 2010 Proc Natl Acad Sci USA 107:7509-7514). Transcription is induced from the $P_I$ promoter in the presence of both ethanolamine and vitamin $B_{12}$, while the promoter $P_{II}$ regulates weak constitutive expression of the transcription factor EutR (Roof and Roth 1992 J Bacteriol 174:6634-6643). (b) Model for catabolism of ethanolamine by the Eut BMC. Ethanolamine enters the microcompartment and is metabolized to ethanol, acetylphosphate and acetyl-CoA, which can enter the tricarboxylic acid cycle (Kerfeld et al. 2010 Annu Rev Microbiol 64:391-408). Eut BMC prevents dissipation of acetaldehyde, a volatile and toxic reaction intermediate (red) (Penrod and Roth 2006 J Bacteriol 188:2865-2874). Enzymes assumed to reside in the BMC lumen include coenzyme-$B_{12}$-dependent ethanolamine ammonia lyase (EAL, EutBC), EAL reactivase (EutA), alcohol dehydrogenase (EutG), aldehyde dehydrogenase (EutE), and phosphotransacetylase (EutD).

Compartmentalized co-localization of enzymes and their substrates represents an attractive approach for multi-enzymatic synthesis in engineered cells and biocatalysis, as it can increase reaction efficiency while also protecting the host cell from potentially toxic reaction intermediates. Several bacteria form protein-based polyhedral microcompartments that sequester functionally related enzymes and regulate their access to substrates and other small metabolites. We expressed putative shell proteins from the *Salmonella enterica* ethanolamine utilization (eut) operon in *E. coli*, and observed the formation of well-defined compartments. Surprisingly, in some embodiments, expression of only one of the shell proteins (EutS) is sufficient and necessary for creating microcompartments and encapsulating heterologous proteins fused to a putative Eut shell-targeting signal sequence. We also demonstrate the functional localization of a model heterologous enzyme (β-galactosidase) targeted to the recombinant shells. Together, our results demonstrate the feasibility of engineering protein nanocompartments for biocatalysis and biosynthesis.

As used herein, the following terms shall have the indicated meanings:

"BMC polypeptide" refers to a structural polypeptide of any naturally-occurring bacterial microcompartment (BMC) including, for example, a carboxysome, an enterosome (e.g., a Pdu BMC or a Eut BMC), and/or a metabolosome (also known as a polyhedral body), whether or not the BMC polypeptide is a component of a BMC, a compartment, or shell as defined herein, or free of any subcellular structure.

"Compartment" or "shell" refers to a recombinant subcellular structure composed of a subset of BMC components, and that defines an environment that is sequestered from the cytoplasm of the cell.

"Compartment-specific" refers to a signal sequence that targets the compound to which the signal sequence is attached for accumulation in a compartment. The signal sequence need not confer absolute specificity. Rather, the signal sequence confers differential, non-random, accumulation of the compound within the compartment.

"Homolog" refers to a BMC polypeptide that is structurally related to the reference BMC polypeptide to which it is a homolog. Homologs of a reference BMC polypeptide may be identified by convention bioinformatic analysis of nucleic acid and/or amino acid databases.

"Isolated" and variations thereof refer to a substance that has been removed from its natural environment to any degree. For instance, an isolated compartment or shell is a compartment or shell, as the case may be, that has been removed from a cell so that many of the cellular polypeptides, nucleic acids, and other cellular material of its natural environment are no longer present. The term "isolated" does not convey any particular degree to which the other cellular components are removed.

"Non-native" refers to any feature of a cell—e.g., a polynucleotide, a polypeptide, or a compartment—that does not occur naturally in that cell. In the context of a compartment, or the proteinaceous shell of a compartment, "non-native" can refer to a compartment or proteinaceous shell that includes one or more heterologous polypeptides or a non-naturally occurring combination of autologous polypeptides. "Heterologous" refers to a feature or component of a cell that originates from a cell of another species. "Autologous" refers to a feature or component of a cell that originates from the cell.

"Polypeptide" refers to a sequence of amino acid residues without regard to the length of the sequence. Therefore, the term "polypeptide" refers to any amino acid sequence having at least two amino acids and includes full-length proteins, truncations of full-length proteins, and chimeric fusions of at least a portion of two or more proteins.

"Targeted enzyme" refers to an enzyme targeted for sequestration in a compartment by a compartment-specific tag.

The term "and/or" means one or all of the listed elements or a combination of any two or more of the listed elements; the terms "comprises" and variations thereof do not have a limiting meaning where these terms appear in the description and claims; unless otherwise specified, "a," "an," "the," and "at least one" are used interchangeably and mean one or more than one; and the recitations of numerical ranges by endpoints include all numbers subsumed within that range (e.g., 1 to 5 includes 1, 1.5, 2, 2.75, 3, 3.80, 4, 5, etc.).

Engineering metabolic pathways into heterologous host cells to produce valuable chemical compounds and biofuels is one goal of synthetic biology (Purnick and Weiss 2009 Nat Rev Mol Cell Biol 10:410-422; Keasling 2008 ACS Chem Biol 3:64-76). Factors such as, for example, diffusion limitation, alternate metabolic routes, and/or accumulation of toxic reaction intermediates and inhibitory products, however, frequently reduce the efficiency of such engineered pathways. In nature, cells often circumvent these issues by co-localizing metabolic enzymes (Lopez-Gallego and Schmidt-Dannert 2010 Curr Opin Chem Biol 14:174-183). Co-localization can be achieved, for example, by tethering enzymes to structures such as protein scaffolds or lipid membranes (Fontes and Gilbert 2010 Annu Rev Biochem 79:655-681; Burbulis and Winkel-Shirley 1999 Proc Natl Acad Sci USA 96:12929-12934). Sequestering enzymes into semi-permeable compartments or organelles is another strategy used by cells to spatially organize metabolic reactions. Compartmentalization can allow more stringent control than, for example, tethering or substrate and product transport to and from enzyme assemblies. Sequestration also can protect the organism from harmful reaction intermediates. Several bacteria form proteinaceous shells that encapsulate functionally related enzymes. These subcellular structures are collectively referred to as bacterial microcompartments (BMCs) (Kerfeld et al. 2010 Annu Rev Microbiol 64:391-408).

BMC shell-encoding genes are present in more than 400 sequenced bacterial genomes and the encoded proteins are often associated with enzymes involved in one of at least eight different metabolic pathways (Kerfeld et al. 2010 Annu Rev Microbiol 64:391-408; Cheng et al. 2008 Bioessays 30:1084-1095; Urano et al. 2010 Appl Microbiol Biotechnol 89:739-746). A subset of BMCs, called carboxysomes, is involved in $CO_2$ fixation (Yeates et al. 2008 Nat Rev Microbiol 6:681-691; Price et al. 2008 J Exp Bot 59:1441-1461). Propanediol utilization (Pdu) BMCs catabolize 1,2-propanediol and are found in, for example, *Salmonella*, *Citrobacter*, and other bacteria (Bobik et al. 1999 J Bacteriol 181:5967-5975; Havemann and Bobik 2003 J Bacteriol 185:5086-5095; Sriramulu et al. 2008 J Bacteriol 190:4559-4567). *Salmonella* spp. can form BMCs during growth on the two-carbon substrate ethanolamine (Kerfeld et al. 2010 Annu Rev Microbiol 64:391-408). Moreover, the membrane constituent phosphatidylethanolamine may serve as a source of carbon, nitrogen, and energy to enteric bacteria (Kerfeld et al. 2010 Annu Rev Microbiol 64:391-408). This view is supported by the attenuated behavior of *Salmonella* ethanolamine utilization (eut) loss-of-function mutants in the murine gut (Stojiljkovic et al. 1995 J Bacteriol 177:1357-1366).

BMC shells can have a viral capsid-like polyhedral structure with a diameter of 100 nm to 150 nm. While the shells of carboxysomes can be icosahedrons, the shells of Pdu and Eut BMCs can be semi-regular polyhedrons. Thin cell-section transmission electron micrographs of Eut BMCs indicate that Eut BMC shells can adopt a rounder, less-sharp-edged morphology than either carboxysomes or Pdu BMCs (Brinsmade et al. 2005 J Bacteriol 187:8039-8046; Shively et al. 1998 Can J Bot 76:906-916).

BMC shells are formed by thousands of copies of a few proteins belonging to the BMC-domain family (Pfam family: Pf00936). BMC-domain proteins have been crystallized as flat cyclic hexamers (or pseudohexamers), and are believed to form the edges and facets of the microcompartment (Yeates et al. 2011 Curr Opin Struct Biol 2011:21). The vertices of these shells may be capped by members of another BMC shell-associated protein family, some of which have been crystallized as pentamers (Pfam family: Pf03319) (Kerfeld et al. 2010 Annu Rev Microbiol 64:391-408). The multimeric shell protein structures can have central pores of varying sizes and with different electrostatic properties. Crystallization of a few shell proteins with their central pores in either "open" or "closed" configuration suggests that they may function as gated transit points for cofactors and small metabolites (Yeates et al. 2011 Curr Opin Struct Biol 2011:21).

To demonstrate the general feasibility of engineering heterologous protein-based microcompartments in a heterologous host cell, we chose to engineer the Eut BMC shell proteins from *Salmonella enterica* LT2 into *E. coli* as a model. While the exact composition of *S. enterica* Eut BMCs is unknown, they are believed to be composed of five shell proteins—i.e., EutS, EutM, EutN, EutL, and EutK. Putative signal sequences that target enzymes to the interior of Eut BMCs can be inferred from BMC-targeting sequences of native Pdu BMCs in *S. enterica* (Fan et al. 2010 Proc Natl Acad Sci USA 107:7509-7514). The Eut BMC shell genes are encoded on the 17-gene eut operon, which also encodes enzymes involved in the degradation of ethanolamine (FIG. 1) (Kofoid et al. 1999 J Bacteriol 181:5317-5329). *S. enterica* Eut BMCs may prevent dissipation of the volatile reaction intermediate acetaldehyde and protect the cell from aldehyde toxicity (Penrod and Roth 2006 J Bacteriol 188:2865-2874; Cheng et al. 2008 Bioessays 30:1084-1095; Brinsmade et al. 2005 J Bacteriol 187: 8039-8046). A homologous eut operon is also present in *E. coli*, but is disrupted by a transposon in several common laboratory strains. Although there have been some reports of eut operon induction and Eut BMC formation in a few *E. coli* strains, these were observed only under very specific growth conditions (Shively et al. 1998 Can J Bot 76:906-916; Bertin et al. 2011 Environ Microbiol 13:365-377). Eut BMCs were not observed in our laboratory *E. coli* strains under either standard growth conditions or conditions reported to induce Eut BMC formation in *S. enterica*. To date, functional characterization of the eut operon has been conducted mainly using *S. enterica*.

While there is interest in engineering bacterial microcompartments to create intracellular protein compartments for biotechnological applications, the interactions between individual BMC shell proteins and enzymes targeted for encapsulation have not been studied in any heterologous system (Fan et al. 2010 Proc Natl Acad Sci USA 107:7509-7514; Yeates et al. 2008 Nat Rev Microbiol 6:681-691; Papapostolou and Howorka 2009 Mol Biosyst 5:723-732). Previously, an attempt was made to produce empty *Citrobacter* Pdu BMCs by overexpressing the Pdu shell proteins in *E. coli*; isolation of intact microcompartments was not reported, however (Parsons et al. 2010 Mol Cell 38:305-315).

Here, we show that a model host cell can form polyhedral microcompartments with recombinantly expressed model BMC shell proteins. Isolated recombinant Eut BMCs produced in model host cell *E. coli* appear to be morphologically similar to the native *S. enterica* Eut compartments. We further demonstrate that an N-terminal signal sequence targets model cargo proteins—e.g., Enhanced Green Fluorescent Protein (EGFP) and β-galactosidase—to the recombinant compartments. The ability to sequester catalytically active β-galactosidase indicates that the recombinant BMCs may be engineered to encapsulate multi-enzymatic reactions. We also report the surprising discovery that one of the BMC-domain proteins, EutS, can be necessary and sufficient for the formation of shells in vivo, and for targeting of heterologous proteins to these structures, thereby offering a simple strategy for the engineering of protein-based nano-bioreactors.

In order to demonstrate that Eut shell proteins are an effective model for heterologous BMC assembly, we established that the Eut shell proteins were expressed by a model heterologous host cell and that the expressed Eut shell proteins could form polyhedral microcompartments in the heterologous host cell.

Expression of Model BMC Proteins (S. Enterica Eut Shell Proteins) in a Model Host Cell (E. coli).

The eut operon in S. enterica encodes for a Pfam03319 protein (EutN) and four BMC-domain proteins (EutS, EutM, EutL and EutK; Pfam00936) which are homologs of Eut and Pdu BMC shell-associated proteins from E. coli and Citrobacter (Yeates et al. 2010 Annu Rev Biophys 39:185-205). We cloned the S. enterica Eut shell genes into expression vector pUCBB (FIG. 8) (Shetty et al. 2008 J Biol Eng 2:5). In 3-dimensional (3-D) crystals, wild type EutS displays a hexameric structure with a bend of approximately 40°, while the EutS-G39V mutant forms flat symmetric hexamers (Tanaka et al. 2010 Science 327:81-84). To determine whether the bent structure foamed by wild type EutS is important for its role in BMC shell function, the EutS-G39V mutant was also functionally characterized in this study. As shown in FIG. 9, EutS, EutS-G39V, EutM, and EutK were overexpressed as soluble proteins in two different E. coli strains, while the expression of recombinant EutN and EutL varied between the two strains. The soluble expression of EutL and EutK was also affected by the co-expression of other Eut shell proteins. EutS and EutM showed aberrant SDS-PAGE migration ("smearing") typical of proteins that have hydrophobic peptide stretches (Rath et al. 2009 Proc Natl Acad Sci USA 106:1760-1765).

Formation of Polyhedral Microcompartments in E. coli Model Host Cell Co-Expressing all Five BMC Model Eut Shell Proteins.

Next, we established that the recombinant Eut shell proteins formed clearly demarcated protein compartments in E. coli. For this purpose, cultures of E. coli harboring all five S. enterica Eut shell genes were grown overnight at 30° C. This lower temperature was expected to reduce the expression of individual recombinant proteins, and supply sufficient time for assembly of the 3-D shell. The cells were fixed, sectioned, and their internal structures examined by transmission electron microscopy (TEM). Expression of all five Eut shell proteins in E. coli resulted in the creation of clearly discernible protein shells in most of the examined cells (Table 1). The observed protein shells bore a strong resemblance to the BMCs produced by S. enterica control cells growing on ethanolamine (FIG. 2a-d, FIG. 10). The recombinant compartments were 100 nm to 200 nm in diameter, well within range of the dimensions reported for native Eut BMCs (Kerfeld et al. 2010 Annu Rev Microbiol 64:391-408). However, while S. enterica cells displayed several Eut BMCs distributed throughout the cell, the recombinant EutSMNLK structures were restricted to only one or two per E. coli cell. These recombinant microcompartments were observed in two different strains of E. coli (C2566 and JM109), thereby demonstrating that their formation is not strain-specific. The EutSMNLK shells were enveloped by an electron-transparent region which was also observed around many of the native S. enterica Eut BMCs. The Eut compartments may therefore be enveloped by a matrix that is removed by detergent wash, suggesting that the matrix may exhibit a lipophilic nature.

EutS Alone is Able to Form Microcompartments in E. Coli.

Based on the crystal structures of Eut shell proteins, a model has been proposed for their assembly to form the microcompartment (Tanaka et al. 2008 Science 319:1083-1086; Tanaka et al. 2010 Science 327:81-84). According to this model, the edges and facets of the shell are formed by EutS and EutM respectively, while the central pore of the EutL pseudohexamer may facilitate gated transport into and out of the BMC. EutN may "cap" the vertices of the icosahedral capsid. Unlike many other Pfam03319 proteins, which form pentamers, EutN crystallizes as a hexamer. The role of EutK in the Eut microcompartment assembly and function is currently unclear.

Figure 2:
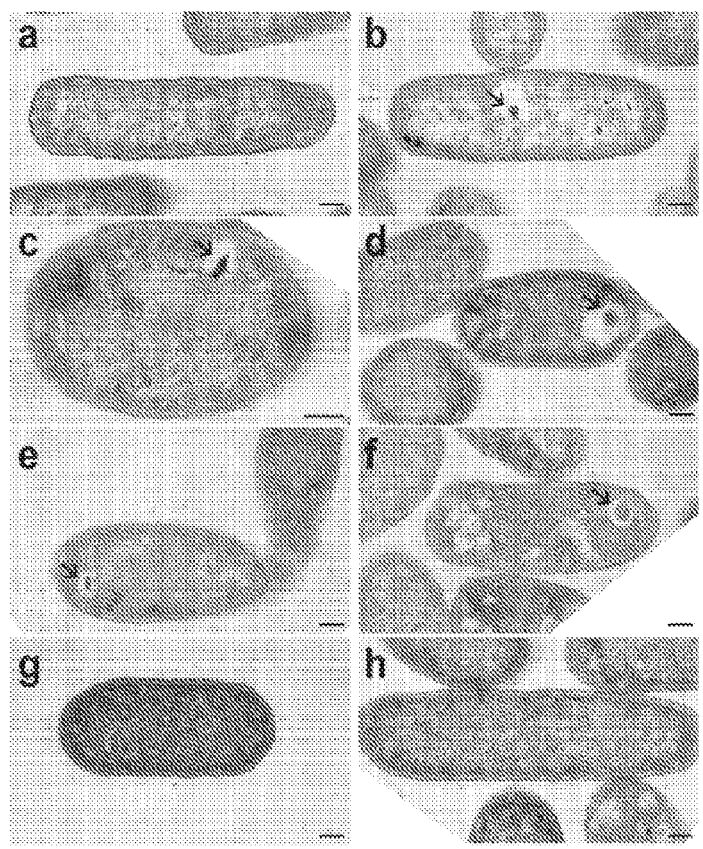
FIG. 2. Formation of microcompartments by expression of *S. enterica* Eut shell proteins in *E. coli*. Transmission electron micrographs of thin sections of *S. enterica* and recombinant *E. coli*. (a) *S. enterica* grown on glycerol. (b) *S. enterica* grown on ethanolamine. (c) *E. coli* C2566 expressing recombinant EutSMNLK. (d) *E. coli* JM109 expressing recombinant EutSMNLK. (e) *E. coli* C2566 expressing recombinant EutS. (f) *E. coli* JM109 expressing recombinant EutS. (g) *E. coli* C2566 expressing recombinant EutMNLK. (h) *E. coli* JM109 expressing recombinant EutMNLK. Arrows indicate the location of recombinant protein compartments. (Scale bar: 200 nm).
Figure 10:
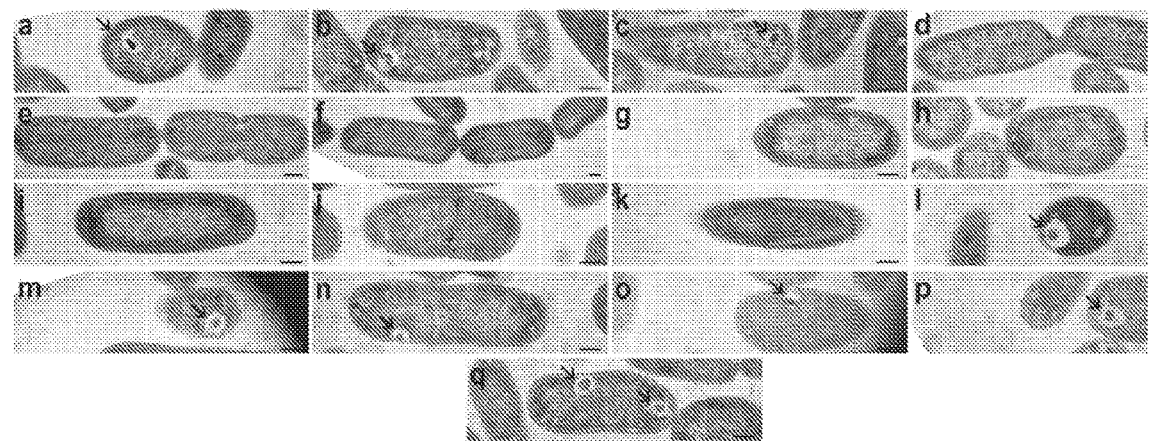
FIG. 10. Transmission electron micrographs of thin sections of recombinant *E. coli* expressing *S. enterica* Eut shell proteins. (a-c) *E. coli* expressing recombinant EutS contain properly delimited microcompartments (*E. coli* strain used in a: C2566, and in b, c: JM109). (d-f) *E. coli* expressing recombinant EutM form thick axial filaments that interfere with separation after cell-division (*E. coli* strain used in d, e: C2566, and in f: JM109). (g) *E. coli* JM109 expressing recombinant EutN. (h) *E. coli* JM109 expressing recombinant EutL. (i) *E. coli* JM109 expressing recombinant EutK shows an electron translucent region in the middle of the cell. (j) An electron dense region is visible in *E. coli* JM109 co-expressing recombinant EutM and EutN. (k) Intracellular filaments are formed in *E. coli* JM109 co-expressing recombinant EutL and EutK. (l-n) Clearly defined microcompartments are observed in *E. coli* JM109 expressing recombinant EutSMNLK. (o-q) Co-expression of EutSMNLK and EutC$^{1-19}$-EGFP results in the formation of compartments that are morphologically similar to the capsids observed in vivo by expression of either EutS or EutSMNLK alone. (*E. coli* strain used in o: C2566, and in p, q: JM109). Arrows indicate the location of recombinant microcompartments. (Scale bar: 200 nm).

To explore the roles of S. enterica Eut shell proteins in the assembly of the Eut microcompartment, they were expressed in E. coli both individually and in different combinations. To our surprise, recombinant expression of EutS alone resulted in the formation of microcompartments which were similar to those observed with EutSMNLK (FIG. 2e-f, FIG. 10). EutS shells appeared to be morphologically similar to the EutSMNLK shells—they too were well-delimited, displayed sharp edges, and were surrounded by an electron-transparent region. One to two polyhedral bodies were observed per cell, and their appearance and localization matched that of compartments produced by EutSMNLK in E. coli. The ratio of 90 nm thin cell sections displaying recombinant shells indicates that a majority of the E. coli cells expressed EutS compartments (Table 1). As shown in FIG. 2g-h, clearly defined structures were not observed in cells co-expressing EutMNLK. These results indicate that engineering of S. enterica EutS can be sufficient to form recombinant microcompartments in E. coli.

Structures formed by over-expression of other Eut shell proteins are shown in FIG. 10. Recombinant expression of EutM alone created a thick axial filamentous structure which allowed cell division but interfered with separation. Similar fibers have been reported in E. coli expressing Citrobacter freundii PduAB, as well as the S. enterica pduJ deletion mutant (Parsons et al. 2010 Mol Cell 38:305-315; Cheng et al. 2011 J Bacteriol 193:1385-1392). Expression of EutK alone resulted in the formation of an electron-translucent region within the cell, while an electron-dense region was produced by co-expression of EutM and EutN. Comparable amorphous aggregates, albeit of a smaller size, are formed by S. enterica pduBB' loss-of-function mutants (Cheng et al. 2011 J Bacteriol 193:1385-1392). A small fraction of cells co-expressing EutLK displayed internal filaments similar to those observed in E. coli expressing Citrobacter PduABKN (Parsons et al. 2010 Mol Cell 38:305-315). Apart from a few polar granules, E. coli expressing either EutN or EutL alone did not display clearly discernible structures.

An N-Terminal Signal Sequence Targets EGFP to BMC Protein Compartments.

Figure 3:
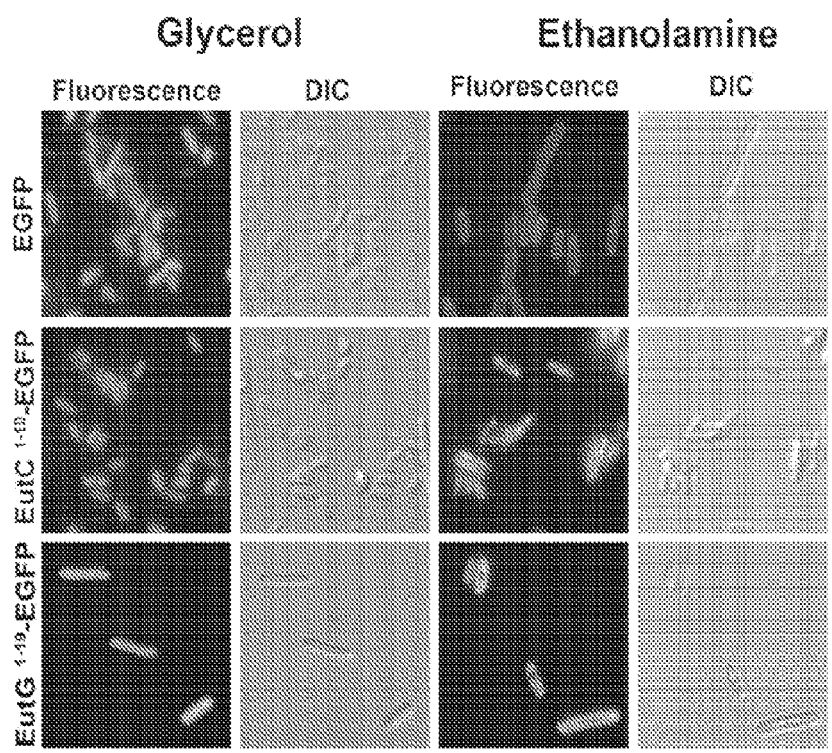
FIG. 3. Distribution of EGFP bearing putative N-terminal Eut BMC-targeting signal sequences in *S. enterica*. *S. enterica* cells containing constructs for constitutive expression of EGFP, EutC$^{1-19}$-EGFP or EutG$^{1-19}$-EGFP were cultured with either glycerol or ethanolamine. Distribution of green fluorescence within the cells was observed by fluorescence microscopy. DIC images show the cell boundaries.

An N-terminal signal sequence of PduP, a Pdu BMC-associated enzyme, targets heterologous proteins to the interior of native Pdu BMC microcompartments in S. enterica (Fan et al. 2010 Proc Natl Acad Sci USA 107:7509-7514). Sequence analysis identified possible N-terminal targeting sequences for other BMC lumen-associated proteins, including EutC and EutG (FIG. 1). In order to determine which, if either, identified signal sequences (the first nineteen amino acids of EutC and EutG, EutC$^{1-19}$ and EutG$^{1-19}$, respectively) indeed function as a Eut BMC-targeting sequences, we made a EutC$^{1-19}$-EGFP fusion and a EutG$^{1-19}$-EGFP fusion and expressed the fusion proteins in S. enterica grown in the presence of either ethanolamine (to induce BMC formation) or glycerol. Bright fluorescent localization was observed in cells expressing the EutC$^{1-19}$-EGFP fusion when the cells were grown on ethanolamine, suggesting that the tagged EGFP was being targeted to the Eut BMCs (FIG. 3). Moreover, the fluorescent loci were not stationary but moved within cells, suggesting interaction of the Eut BMCs with the S. enterica cytoskeleton.

No fluorescent localization was observed in cells expressing the EutC$^{1-19}$-EGFP fusion when the cells were grown on glycerol, or with the EGFP control. Cells expressing EutG$^{1-19}$-EGFP also failed to display punctate green fluorescence when grown on ethanolamine, indicating that fusion with the first nineteen amino acids of EutG is not sufficient to target heterologous proteins to the Eut BMC.

Figure 4:
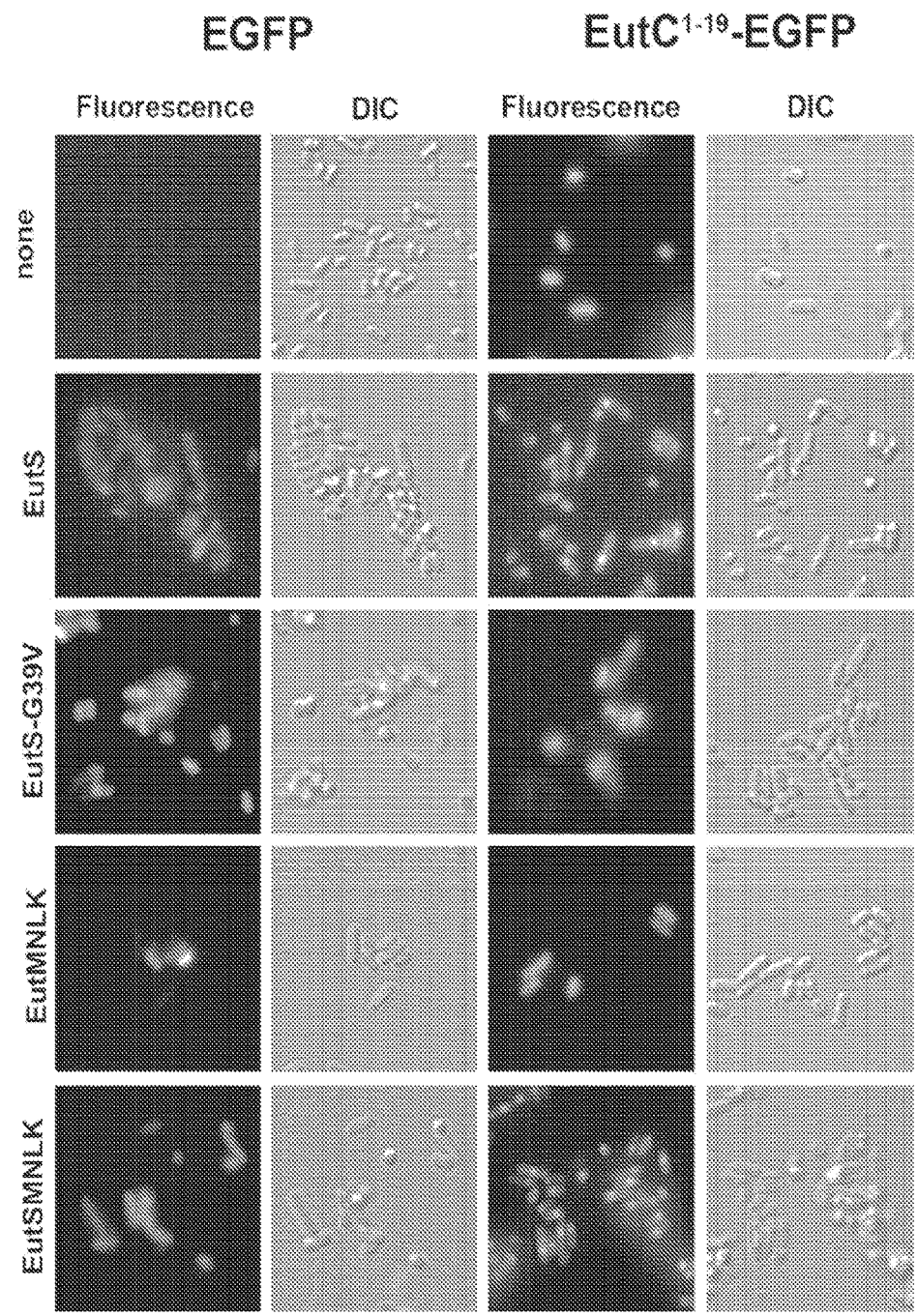
FIG. 4. Localization of EutC$^{1-19}$-EGFP in recombinant *E. coli* expressing *S. enterica* Eut shell proteins. Fluorescence microscopy images of *E. coli* C2566 cells co-expressing EGFP or EutC$^{1-19}$-EGFP with EutS (wild type or the G39V mutant), EutMNLK or EutSMNLK. Cell boundaries are shown by the DIC images. See Table 1 for the quantification of EGFP localization in recombinant *E. coli*, and FIG. 11 for the localization of EutC$^{1-19}$-EGFP in the *E. coli* JM109 strain.
Figure 11:
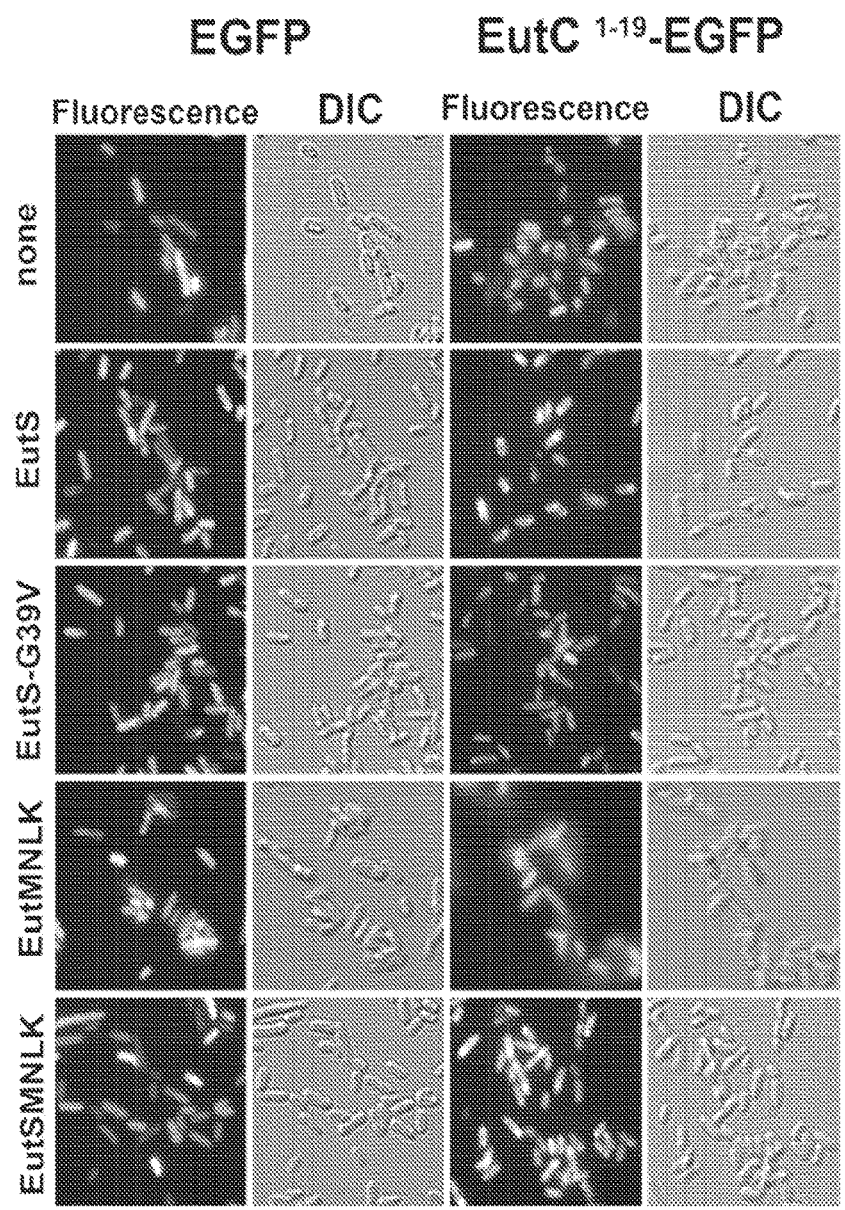
FIG. 11. Localization of EutC$^{1-19}$-EGFP in recombinant *E. coli* JM109 cells expressing *S. enterica* Eut shell proteins. Fluorescence microscopy images of *E. coli* JM109 cells co-expressing EGFP or EutC$^{1-19}$-EGFP with EutS (wild type and the G39V mutant), EutMNLK or EutSMNLK. See Table 1 for the quantification of EGFP localization in recombinant *E. coli*, and FIG. 4 for the localization of EutC$^{1-19}$-EGFP in the *E. coli* C2566 strain. Cell boundaries are shown by the DIC images.

After establishing that the first nineteen amino acids of EutC functioned as a BMC-targeting sequence in *S. enterica*, we explored whether this sequence also localized heterologous proteins to the recombinant Eut shells engineered in *E. coli*. Therefore, EutC$^{1-19}$-EGFP was expressed in *E. coli* cells harboring the entire complement of Eut BMC shell proteins (EutSMNLK). Strong localized fluorescence was observed in 84% of the recombinant *E. coli* C2566 cells (FIG. 4, Table 1). Fluorescent green foci also were observed by co-expression of EutC$^{1-19}$-EGFP and EutSMNLK in *E. coli* JM109 cells, which indicates that the effect is not strain-specific (FIG. 11, Table 1). The number and location of these fluorescent foci (one to two per cell, near the poles) are consistent with the capsid structures observed by transmission electron microscopy (TEM). Transmission electron micrographs of thin cell sections indicated that similar structures were formed by *E. coli* cells expressing recombinant EutSMNLK alone or in combination with EutC$^{1-19}$-EGFP, supporting the observation that formation of the BMC in vivo does not require scaffolding provided by a cargo protein (FIG. 10) (Parsons et al. 2010 Mol Cell 38:305-315; Menon et al. 2008 PLoS One 3:e3570). Unlike in *S. enterica*, fluorescent loci in *E. coli* cells co-expressing EutSMNLK with EutC$^{1-19}$-EGFP appeared to be stationary.
EutS can be Sufficient and Necessary for Targeting EutC$^{1-19}$-EGFP to Recombinant Eut Compartments.

Figure 12:
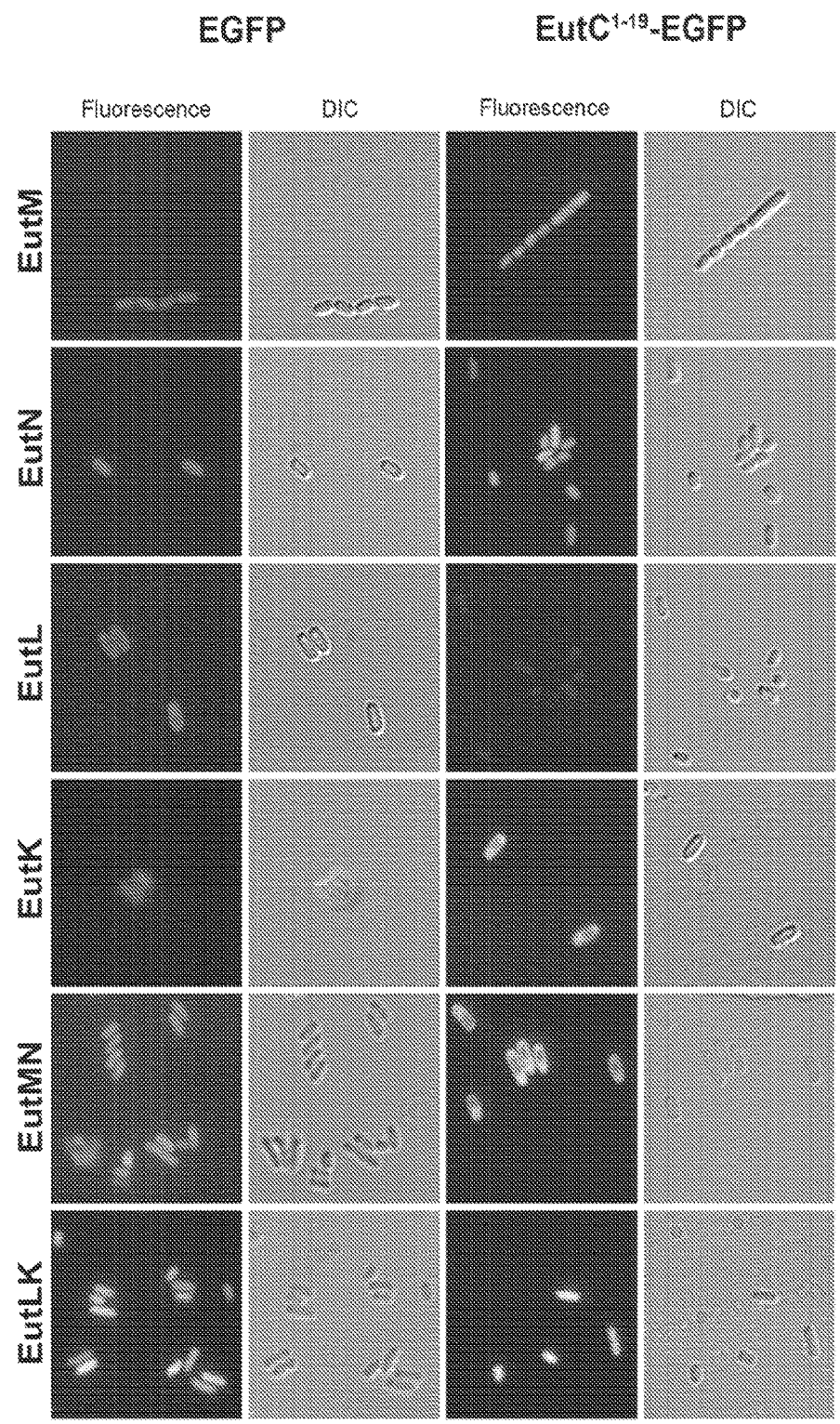
FIG. 12. Localization of EutC$^{1-19}$-EGFP in recombinant *E. coli* C2566 cells expressing various combinations of *S. enterica* Eut shell proteins. Fluorescence microscopy images of *E. coli* C2566 cells with constructs for constitutive expression of EGFP or EutC$^{1-19}$-EGFP with EutM, EutN, EutL, EutK, EutMN and EutLK. In the absence of EutS, there is no discrete fluorescent localization of EutC$^{1-19}$-EGFP, which indicates that EutS is required for targeting EutC$^{1-19}$-EGFP to the engineered microcompartments. Cell boundaries are shown by the DIC images.

To investigate whether one Eut shell protein or a combination of Eut shell proteins is required for EGFP localization in *E. coli*, we next co-expressed EutC$^{1-19}$-EGFP with various Eut shell proteins. Remarkably, co-expression of only EutS and EutC$^{1-19}$-EGFP resulted in the formation of fluorescent foci within 87% of the *E. coli* C2566 cells and 84% of the *E. coli* JM109 cells, while cells expressing the EutS-G39V mutant or other Eut shell protein combinations without wild type EutS did not display discrete fluorescent localizations (FIG. 4, FIG. 11, FIG. 12, Table 1). Our results therefore indicate that, in certain embodiments, EutS can be necessary and sufficient for targeting EutC$^{1-19}$-EGFP to the engineered microcompartment.
EutS and EutSMNLK Shells are Neither Inclusion Bodies Nor are they Enveloped by a Hydrophobic Matrix.

Figure 13:
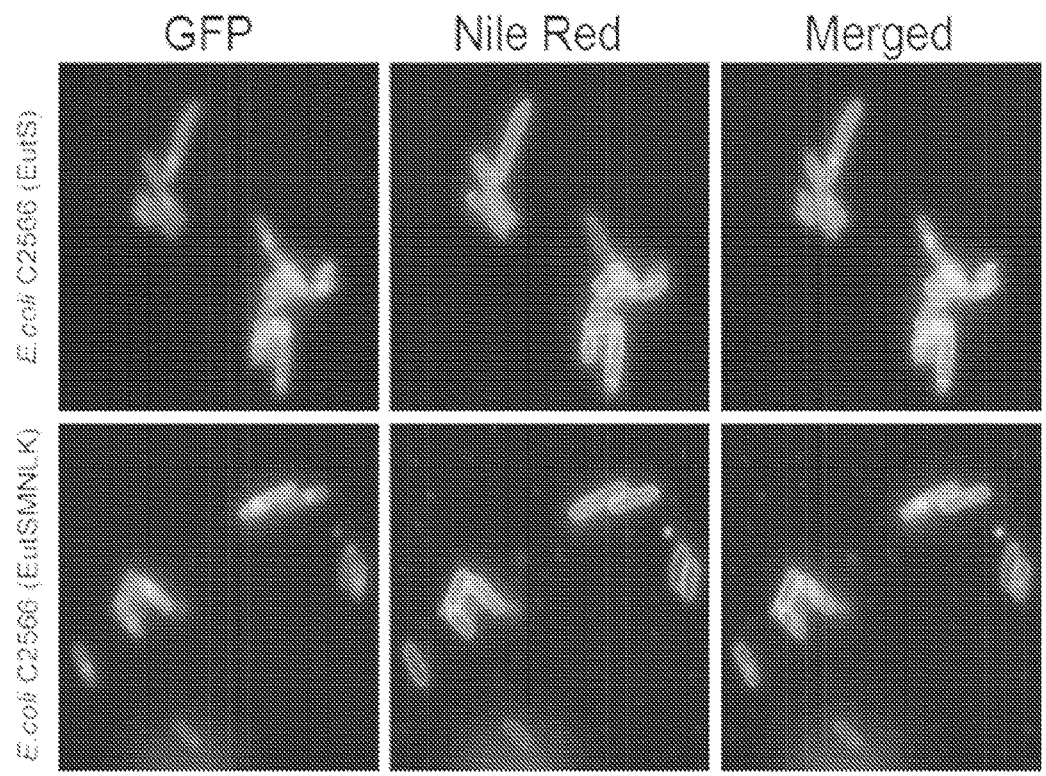
FIG. 13. Nile Red staining of recombinant *E. coli* expressing EutC$^{1-19}$-EGFP. *E. coli* C2566 cells co-expressing EutC$^{1-19}$-EGFP and EutS or EutSMNLK were stained with the fluorescent, lipophilic inclusion body stain Nile Red. Co-localization of red and green fluorescence was not observed, indicating that the recombinant Eut shells are not inclusion bodies nor are the surrounded by a hydrophobic matrix.
Figure 14:
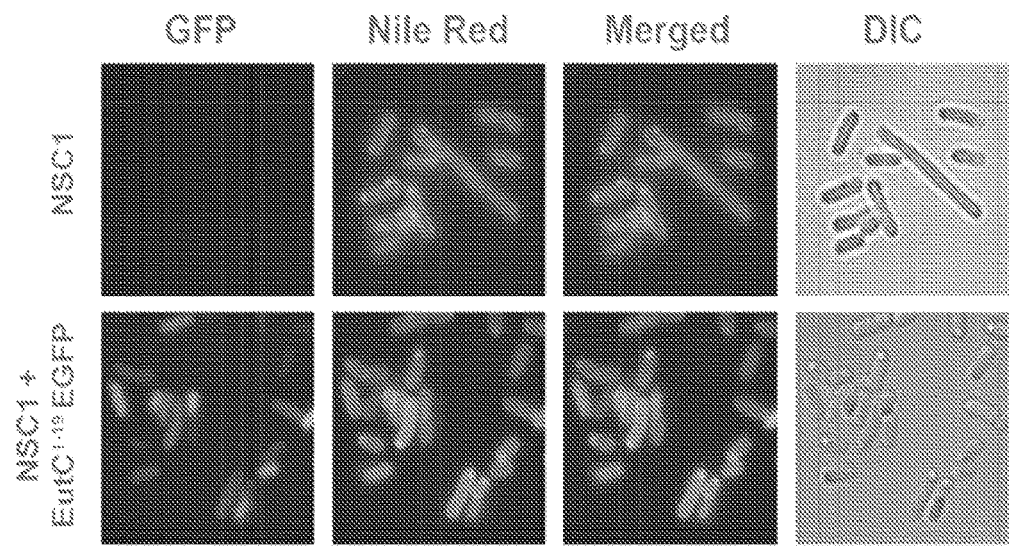
FIG. 14. Nile Red staining of recombinant *E. coli* expressing NSC1. *E. coli* C2566 cells co-expressing the cyanobacterial carotenoid cleavage dioxygenase NSC1 either alone or with EutC$^{1-19}$-EGFP. While red fluorescent puncta corresponding to inclusion bodies were observed in the presence of NSC1, co-localization of red and green fluorescence was not seen, showing that EutC$^{1-19}$-EGFP is not targeted to NSC1 inclusion bodies.

The red fluorescent, lipophilic stain Nile Red was employed to examine the composition of the matrix surrounding the engineered proteins shells and to confirm that the shells were not inclusion bodies (Steinmann et al. 2010 Appl Environ Microbiol 76:5563-5569). *E. coli* cells co-expressing EutC$^{1-19}$-EGFP and Eut shell proteins were stained with Nile Red, reasoning that co-localization of red and green fluorescent foci would indicate that the observed shells are either enveloped by a hydrophobic layer or are made up of aggregated, mis-folded proteins—i.e., inclusion bodies. As shown in FIG. 13, no such co-localization was observed, indicating that the engineered protein shells fouled by EutS alone or EutSMNLK are not inclusion bodies nor are they surrounded by a lipophilic matrix. As a control, we stained with Nile Red *E. coli* cells co-expressing the cyanobacterial carotenoid cleavage dioxygenase NSC-1, which we have previously shown to form inclusion bodies (Marasco et al. 2006 J Biol Chem 281:31583-31593), and EutC$^{1-19}$-EGFP. Nile Red deposits were observed in *E. coli* expressing NSC1 inclusion bodies (FIG. 14). Furthermore, we observed dispersed green fluorescence, indicating that EutC$^{1-19}$-EGFP is not targeted to the NSC1 inclusion bodies. Therefore, our results indicate that overexpressed EutS or EutSMNLK do not form inclusion bodies in *E. coli* nor are the shells enveloped by a hydrophobic layer. The composition of the matrix surrounding the shells (appearing as electro-transparent region after detergent wash) remains unclear.

The localization of EutC$^{1-19}$-EGFP but not EGFP to either EutS or EutSMNLK protein shells also shows that the recombinant protein shells are made of functional, properly folded proteins and are not merely aggregates of mis-folded proteins. Further evidence for the protein shells not being inclusion bodies is provided by the absence of EutC$^{1-19}$-EGFP puncta in *E. coli* cells co-expressing the EutS-G39V mutant (FIG. 4, FIG. 11, Table 1). Crystallographic studies show that this particular mutation changes the conformation adopted by EutS hexamers (Tanaka et al. 2010 Science 327:81-84). Our data links the altered 3-D crystal structure of EutS-G39V with an inability to sequester EutC$^{1-19}$-EGFP, suggesting that the conformation adopted by properly folded EutS-WT in vivo is involved in targeting EutC$^{1-19}$-EGFP to the engineered protein shell.
Isolation of Eut Microcompartments.

To further characterize Eut microcompartment formation in *E. coli*, we isolated the recombinant compartments. To the best of our knowledge, no one has previously reported successfully isolating *S. enterica* Eut microcompartments. We therefore first established a protocol for isolating native Eut BMCs from *S. enterica* grown on ethanolamine. To assist in tracking fractions containing Eut BMCs during ultracentrifugation steps, we used *S. enterica* cells expressing EutC$^{1-19}$-EGFP, to make encapsulation of EutC$^{1-19}$-EGFP by Eut BMCs visible under UV light. Native Eut compartments were then isolated by modifying a previously established protocol reported for native *S. enterica* Pdu BMCs (Havemann and Bobik 2003 J Bacteriol 185:5086-5095). As a negative control we performed the same isolation procedures with *E. coli* C2566 cells expressing only EutC$^{1-19}$-EGFP.

A white band that was fluorescent under UV light after sucrose gradient ultracentrifugation of *S. enterica* cell lysate was collected for further analysis. The *E. coli* EutC$^{1-19}$-EGFP control revealed a faint white band, but no fluorescent bands, in the sucrose gradient that was also collected. Isolated fractions were then analyzed by SDS-PAGE and TEM. SDS-PAGE analysis of the *Salmonella* sample (FIG. 5A, lane 1) showed a number of protein bands, including bands with molecular weights expected for recombinant Eut compartment proteins and EGFP (FIG. 9). Aberrant protein migration ("smearing") of low molecular weight bands occurred similar to what was previously seen with the expression of EutS and EutM in *E. coli*. SDS-PAGE analysis of the control fraction from *E. coli* EutC$^{1-19}$-EGFP did not show any protein bands.

Figure 5:
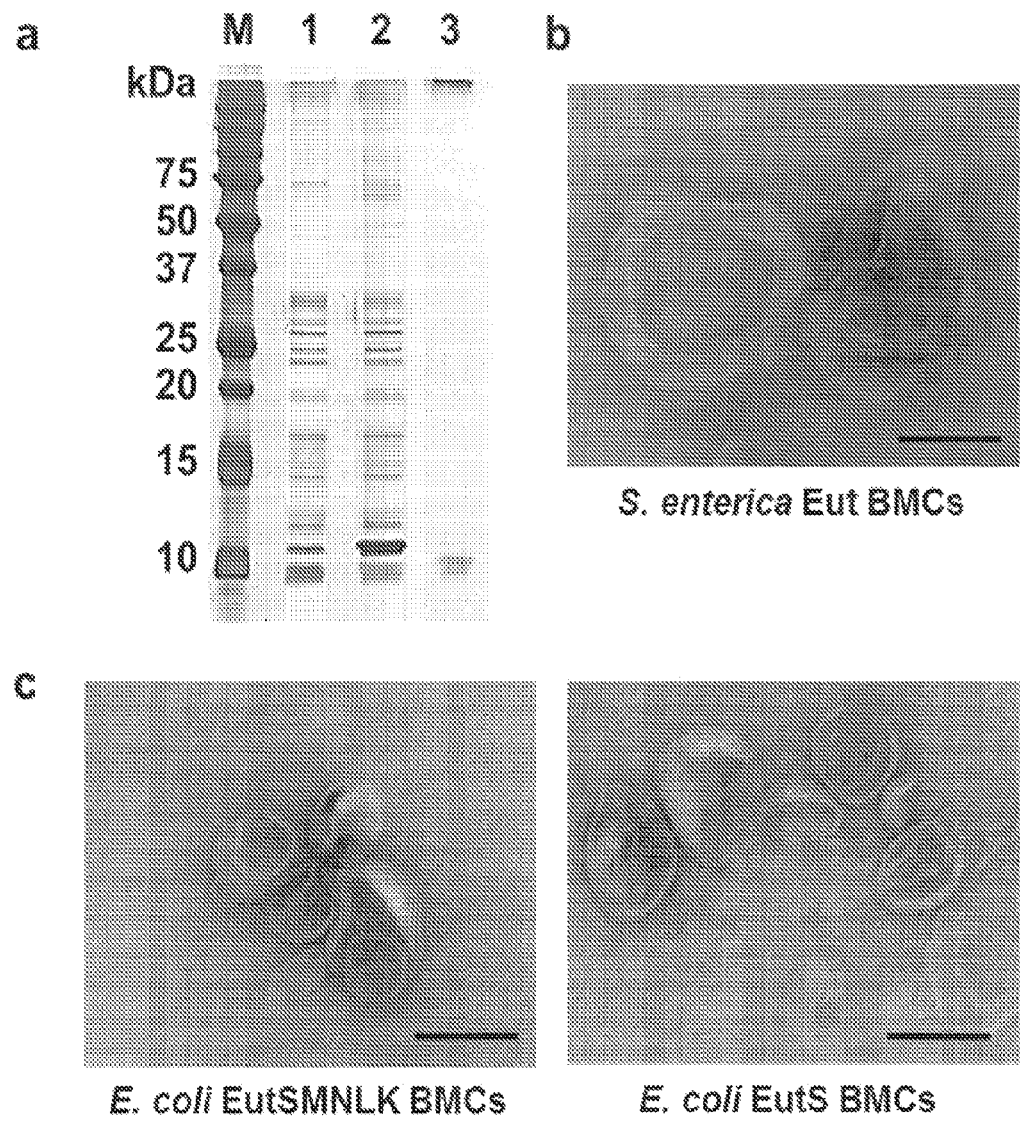
FIG. 5. Isolation of Eut microcompartments. (a) Silver stained SDS-PAGE gel showing isolation of (lane 1) Eut BMCs from *S. enterica* cells harboring EutC$^{1-19}$-EGFP, (lane 2) recombinant EutSMNLK shells, and (lane 3) recombinant EutS compartments from *E. coli* C2566 cells co-expressing EutC$^{1-19}$-EGFP. Calculated protein sizes are as follows: EutS (11.6 kDa), EutM (9.8 kDa), EutN (10.4 kDa), EutL (22.7 kDa), EutK (17.5 kDa), EutC$^{1-19}$-EGFP (29.1 kDa). (b) Transmission electron micrographs of isolated native and recombinant Eut microcompartments from *S. enterica*. (c) Transmission electron micrographs of isolated native and recombinant Eut microcompartments from *E. coli*. From left to right: EutSMNLK shells from *E. coli* C2566, EutS shells from *E. coli* C2566. (Scale bar: 100 nm).

Negative stain TEM of the isolated native Eut organelles revealed structures that were irregular in shape, with dimensions in the range of 100 nm to 150 nm (FIG. 5B). The isolation was reproduced several times and negatively-stained structures of the same morphology were viewed on several different occasions, indicating that the structures isolated and viewed are the native Eut BMCs. The *E. coli* EutC$^{1-19}$-EGFP control sample did not contain any structures that could be visualized by TEM, confirming that the visualized *Salmonella* compartments are Eut BMCs and not membrane vesicles.

As an additional control, native Pdu BMCs from *S. enterica* were also isolated and visualized following the published method (FIG. 15A) (Havemann and Bobik 2003

J Bacteriol 185:5086-5095). The observed morphology of the isolated Pdu and Eut BMCs is very similar—the structures are clearly discernible but somewhat deflated, perhaps as the result of the isolation procedure and/or the dehydration involved in negative stain EM.

Subsequently, we applied the same isolation procedure developed for native Eut BMCs to the isolation of recombinant EutSMNLK and EutS compartments from E. coli C2566 co-expressing EutC$^{1-19}$-EGFP. As with the S. enterica Eut BMCs, a faint UV fluorescent band was detected after sucrose gradient ultracentrifugation and collected for further analysis. SDS-PAGE analysis of the isolated recombinant EutSMNLK compartments (FIG. 5A, lane 2) showed a very similar protein pattern in the expected Eut compartment protein size range when compared to the native Eut BMCs (FIG. 5A, lane 1). Protein patterns differ between the native BMC and recombinant protein compartment preparations in the higher molecular weight range. The isolated EutS compartment showed one smeared band at around 10 kDa as expected for EutS, but no band corresponding to EutC$^{1-19}$-EGFP. This might be due to a low protein concentration. We noticed that a large fraction of the loaded EutS protein does not migrate into the gel, suggesting that it may retain EutC$^{1-19}$-EGFP, thereby rendering its concentration in the gel too low for detection.

TEM analysis of the isolated recombinant EutSMNLK compartments showed that they also appeared to be irregular structures (FIG. 5C). Isolated recombinant EutSMNLK capsids were about 100 nm in diameter and slightly smaller than the native Eut BMCs (FIGS. 5B and 5C). This difference in size may represent a difference in the number of different proteins constituting the native and recombinant compartments. While the native Eut shells are believed to be composed of only five shell proteins, a greater number of proteins may be involved in the formation of Eut BMCs in the native S. enterica host cell. For example, Pdu BMC shells are composed of seven proteins, one of which was only recently verified as a component of the shell (PduN) (Bobik et al. 1999 J Bacteriol 181:5967-5975; Cheng et al. 2011 J Bacteriol 193:1385-1392). The morphology of isolated EutS protein shells was similar to that of EutSMNLK compartments, (FIG. 5C), which supports the conclusion that EutS is capable of forming protein shells on its own.

Figure 15:
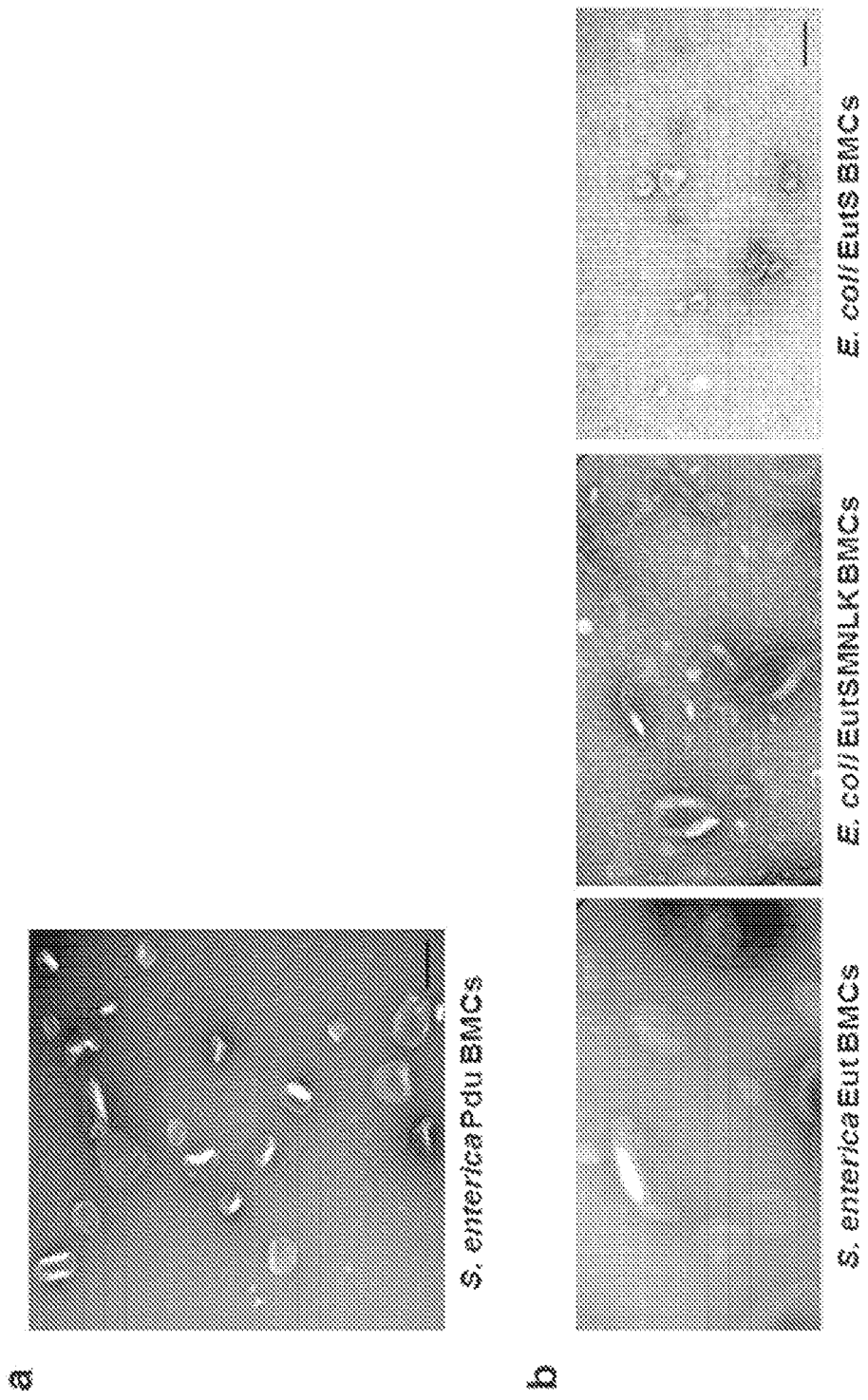
FIG. 15. Transmission electron micrographs isolated protein compartments. (a) Native Pdu BMCs isolated from *S. enterica*. (b) Native Eut BMCs and recombinant Eut protein shells isolated from cells not expressing the cargo protein EutC$^{1-19}$-EGFP. From left to right: Native Eut BMCs isolated from *S. enterica*, recombinant EutSMNLK compartments isolated from *E. coli* C2566, and recombinant EutS shells isolated from *E. coli* C2566. Scale bar: 100 nm.

The isolation was reproducible and was also applied to the partial isolation of native and recombinant Eut shells from cells that do not express EutC$^{1-19}$-EGFP (FIG. 15B). Negative stain TEM indicated that the size and morphology of the isolated native Eut and recombinant EutSMNLK compartments were unaffected by the presence or absence of the cargo protein EutC$^{1-19}$-EGFP. However, empty EutS compartments (isolated from E. coli cells recombinantly expressing EutS only, and not the cargo protein EutC$^{1-19}$-EGFP) appeared to be less able to withstand isolation. Isolated empty EutS shells were observed to be 50 nm in diameter, the samples were less homogeneous, and a number of shells appeared to be broken (FIG. 15B). Empty EutS shells also sedimented differently from the other protein compartments during sucrose gradient centrifugation.

Eut BMC-Targeted EGFP is Sequestered within the Eut Microcompartments.

Figure 6:
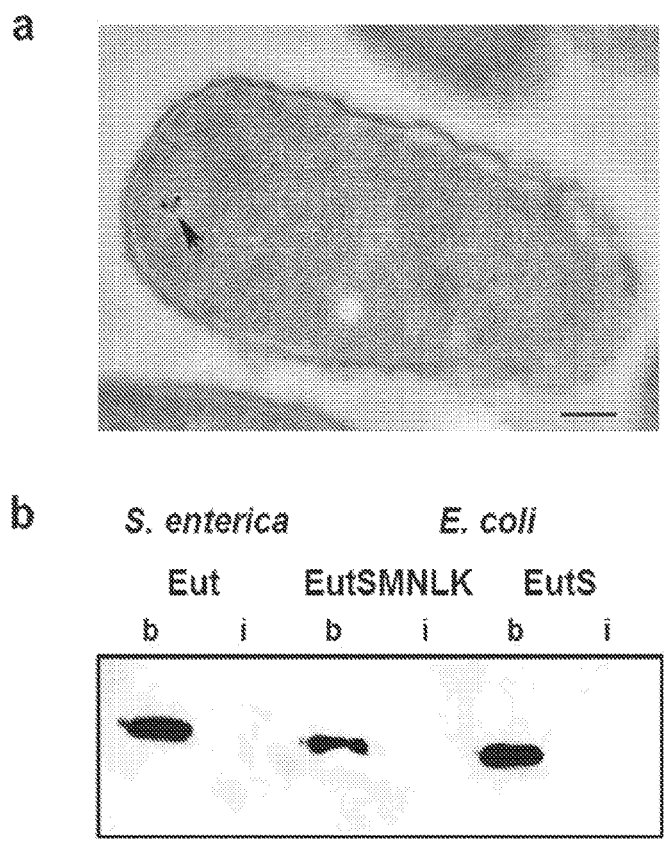
FIG. 6. EutC$^{1-19}$-EGFP is sequestered in the recombinant EutSMNLK compartment. (a) Anti-GFP immunogold TEM of a thin section of *E. coli* JM109 cells co-expressing EutSMNLK and EutC$^{1-19}$-EGFP. Gold particles are localized to a protein shell. (Scale bar: 200 nm). (b) Anti-GFP western blot analysis of broken (b) and intact (i) Eut compartments, harboring EutC$^{1-19}$-EGFP.
Figure 16:
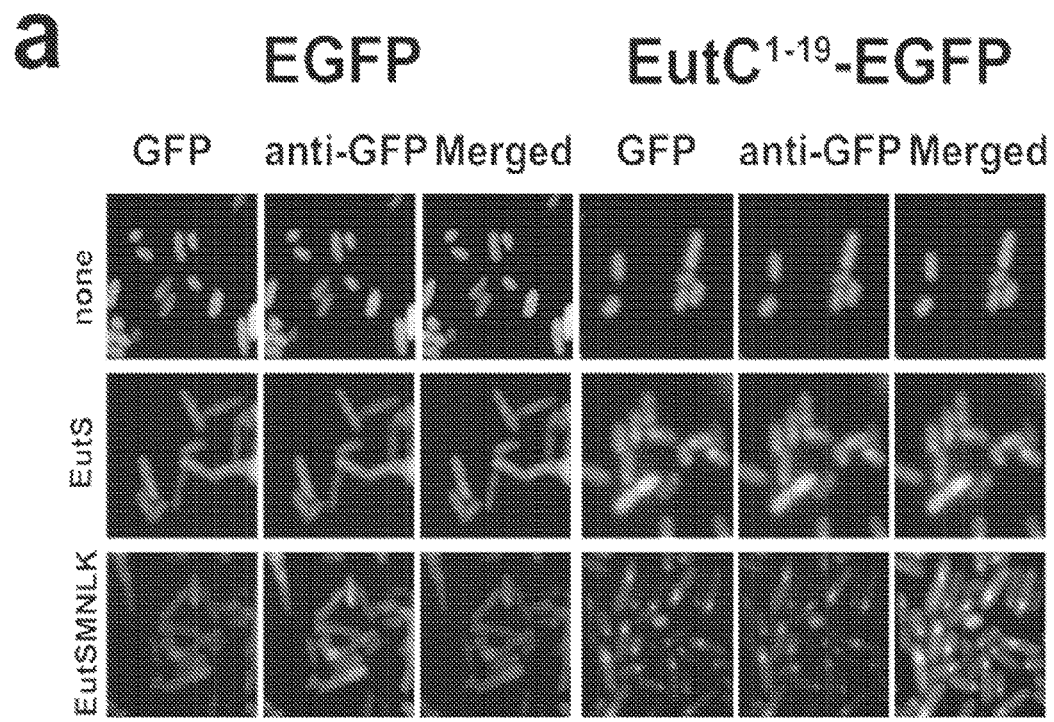
FIG. 16. Immunofluorescence analysis of EutC$^{1-19}$-EGFP localization in recombinant *E. coli* expressing Eut BMC-domain proteins. EGFP, anti-GFP antibody and merged EGFP-anti-GFP antibody fluorescence signals from *E. coli* cells with constructs for constitutive expression of EGFP or EutC$^{1-19}$-EGFP with EutS or EutSMNLK. (a) anti-GFP immunofluorescence studies in the *E. coli* strain C2566. (b) anti-GFP immunofluorescence studies in the *E. coli* strain JM109.
Figure 16:
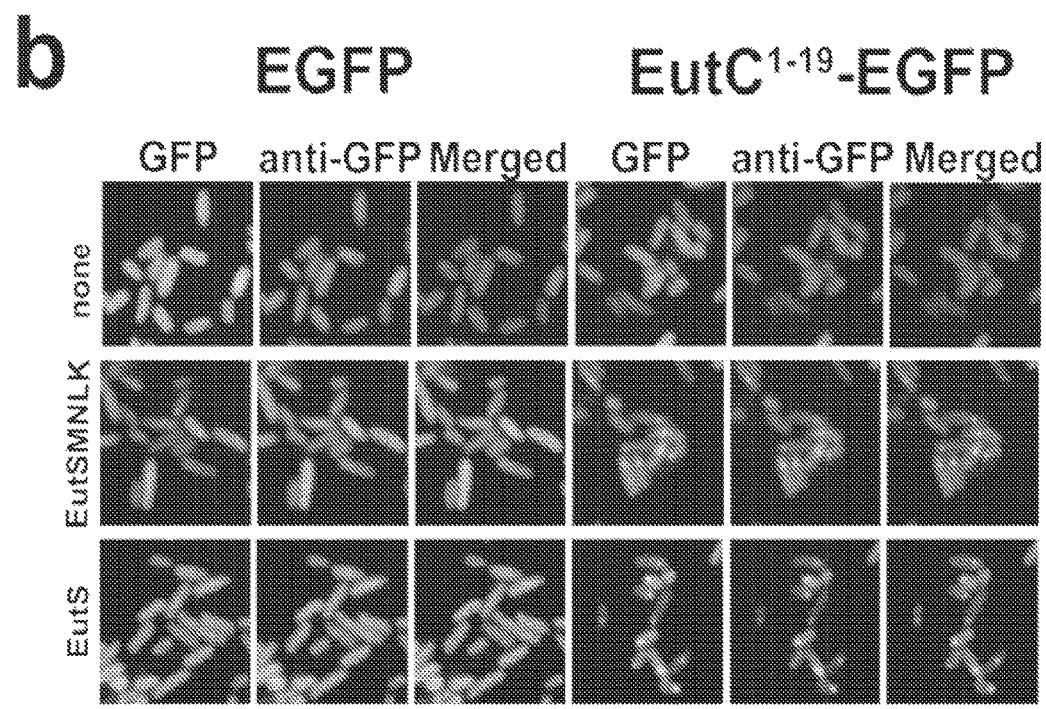

Anti-GFP immunofluorescence studies and anti-GFP immunogold TEM were performed to confirm the localization of EutC$^{1-19}$-EGFP to EutMNLK microcompartments (FIG. 6a, FIG. 16). As shown in FIG. 6a, the anti-GFP immunogold beads co-localize at a discrete polyhedral structure located near the pole of the recombinant E. coli cell, indicating that EutC$^{1-19}$-EGFP is specifically targeted to the EutSMNLK recombinant compartment. We also determined whether EutC$^{1-19}$-EGFP is encapsulated within the engineered protein shells or whether it interacts with the outer surface of the shells. Eut BMCs isolated from S. enterica and E. coli (all co-expressing EutC$^{1-19}$-EGFP) were broken by sonication, and intact and broken microcompartments were incubated with anti-GFP antibodies following a similar procedure recently described for protein localization into native Pdu BMCs (Fan et al. 2010 Proc Natl Acad Sci USA 107:7509-7514). Western blots show that GFP could be detected in broken compartments (native as well as recombinant), but not in intact shells (FIG. 6b). These findings indicate that EutC$^{1-19}$EGFP molecules are encapsulated within both native and recombinant Eut microcompartments (preventing their interactions with anti-GFP antibodies), and are not localized on the outside surface of the Eut protein shells.

Targeting of an Enzyme to the Recombinant Eut Microcompartment.

Figure 7:
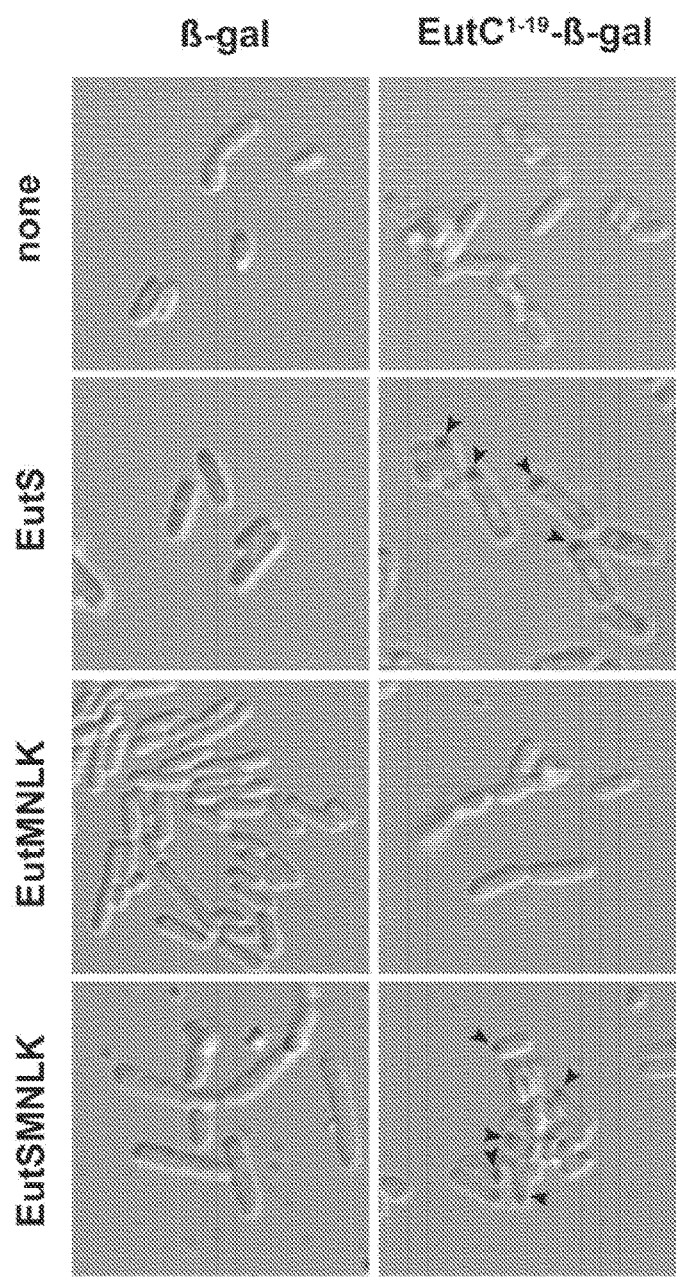
FIG. 7. Hydrolysis of X-gal by *E. coli* co-expressing EutC$^{1-19}$-β-galactosidase and recombinant Eut shell proteins. *E. coli* C2566 cells with constructs for constitutive expression of β-galactosidase (β-gal) or EutC$^{1-19}$-β-gal and different combinations of Eut shell proteins were grown with the β-gal substrate X-gal. Intracellular accumulation of the insoluble X-gal cleavage product was observed by Differential Interference Contrast (DIC) microscopy. Arrows point to intracellular indole deposits.

Finally, to explore the feasibility of developing recombinant Eut shells for enzyme sequestration and catalysis, we chose to study hydrolysis of the chromogenic substrate 5-bromo-4-chloro-3-indolyl-β-D-galactopyranoside (X-gal) by β-galactosidase fused N-terminally with the EutC BMC-targeting sequence. Hydrolysis of X-gal produces an insoluble colored indole (indigo). As shown in FIG. 7, E. coli co-expressing EutC$^{1-19}$-β-galactosidase and either EutS or EutSMNLK displayed discrete accumulation of the colored X-gal cleavage product within the cell. The intracellular location of the colored precipitate was consistent with the localization of EutC$^{1-19}$-EGFP, as well as the location of capsid-like structures observed in TEM. No accumulation of the insoluble indigo product was observed within cells co-expressing EutC$^{1-19}$-β-galactosidase with EutMNLK. Intracellular indole deposits also were absent in cells co-expressing untagged β-galactosidase and Eut shell proteins. Taken together, these data indicate that EutC$^{1-19}$-β-galactosidase is sequestered within the engineered Eut BMC and remains functional.

Table 1 provides data regarding the ratio of E. coli cells exhibiting recombinant Eut compartments. Section I quantifies the distribution of recombinant Eut shells in E. coli by fluorescence microscopy. Section II quantifies the distribution of recombinant Eut compartments in E. coli by TEM. Thin cell sections of E. coli expressing EutS or EutSMNLK were observed by TEM. Assuming an average E. coli cell has a height of 2 μm and a diameter of 0.5 μm, about 20 thin sections (90 nm in width) perpendicular to the axis can be cut from each cell. An average recombinant BMC has a diameter of 100 nm to 200 nm. The average cell would have about 20 cross-sections parallel to the circular base, of which only two would pass through a EutS shell. Even if 100% of E. coli had a recombinant EutS compartment, the actual fraction of cell cross-sections showing the phenotype would be around 10%. For sections parallel to the height of the cell, less than 40% would be expected to display the shell, and the number showing capsids at close to their maximum width will be even lower.

Controlling the Number of Microcompartments Per Cell

Figure 18:
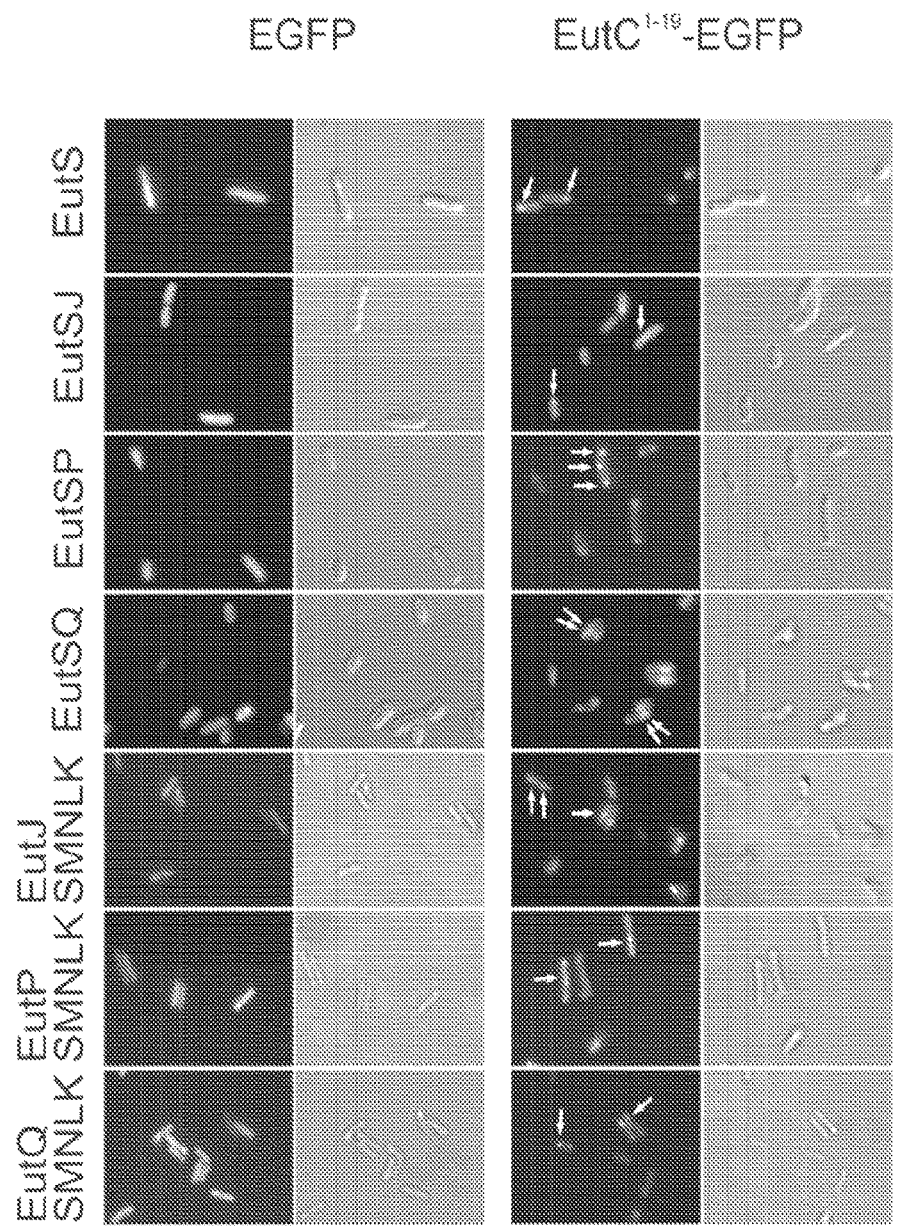
FIG. 18. Novel Eut proteins affect the number of recombinant compartments formed in vivo. Representative fluorescence microscopy images of JM109 *E. coli* cells expressing EutJ, EutP, and EutQ combined with the canonical structural proteins EutS or EutSMNLK. In all cases, these constructs were co-expressed with either EGFP or EGFP tagged with the EutC$^{1-19}$ signal sequence.

The disparity in the number of compartments formed in vivo between the native organism S. enterica and our engineered system in E. coli prompted the investigation of what role other regions of the Eut operon might play during BMC formation. To address this, a number of non-structural Eut proteins with unknown functions (EutJ, EutP, and EutQ) were selected. We constructed engineered circuits combining EutS or EutSMNLK with EutJ, EutP, or EutQ and analyzed BMC formation in vivo. In combination with EutS alone, the number of BMCs formed *E. coli* cells expressing EutP or EutQ increased, with the majority of cells containing more than one BMC per cell, often two or three (FIG. 18). When combined with the entire set of five shell proteins (EutSMNLK), *E. coli* cells expressing EutJ, EutP, or EutQ all formed multiple BMCs per cell in a manner more reminiscent of the native state observed in *S. enterica*.

Figure 20A:
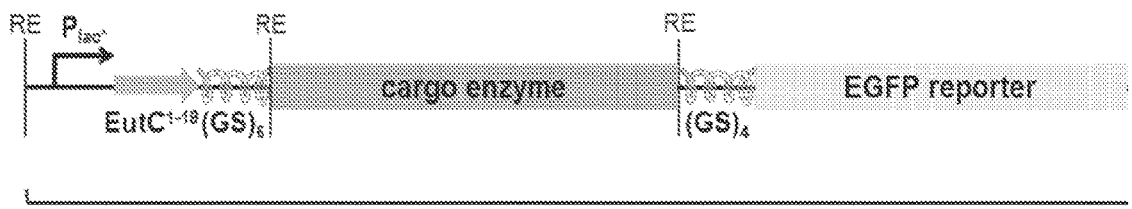
FIG. 20. Modular expression cassettes designed for targeting multiple enzymes into engineered nanocompartments in *E. coli*. (A) Schematic representation of cassette design with promoter, EutC$^{1-19}$ targeting sequence, small peptide linker, cargo enzyme, EGFP reporter and (RE denotes restriction sites flanking modules). (B) Localization of lipase EutC$^{1-19}$-BTL-2 (fused to EGFP using the designed cassette) to EutS compartments in *E. coli*.
Figure 20B:
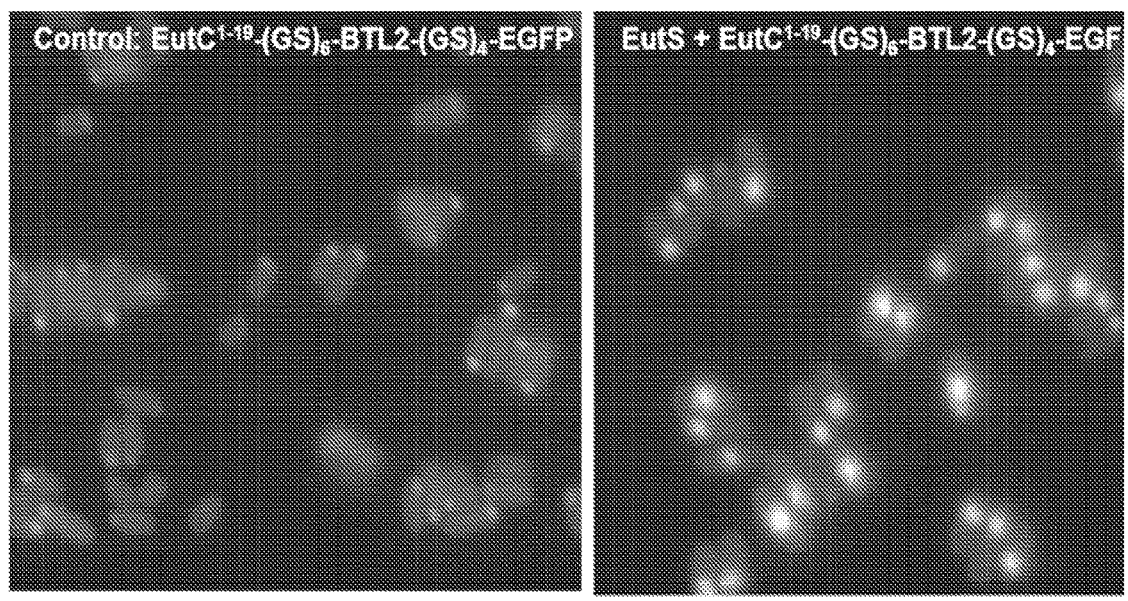

Non-structural proteins such as EutJ, EutP, and EutQ can influence the number of recombinant compartments formed in vivo through yet uncharacterized and unique domains. For example, in silico analysis of EutP revealed similarities to GTPase enzymes, which are an extensive family of proteins with a wide range of function, including directing motility in a cytoskeletal-dependant fashion via ineraction with the prokaryotic actin homologue, MreB (Mauriello et al. 2010 EMBO 29:315-326). EutQ on the other hand is predicted to contain a bi-cupin domain, which is a widely conserved domain amongst both prokaryotes and eukaryotes (Dunwell et al. 2004 Phytochemistry 65:7-17) and has yet to be functionally characterized in the context of prokaryotic microcompartment form and function.

are N-terminally tagged with the $EutC^{1-19}$-BMC targeting sequences followed by either a flexible $(GS)_6$ or helical, rigid $(EAAK)_4$ linker to minimize potential interference of the cargo protein on signal sequence conformation and function. For quick, initial visualization of cargo enzyme targeting into compartments, we added a C-terminal EGFP fluorescent reporter gene fusion via another flexible linker. This fusion can be removed in the final multi-enzyme co-expression construct. We have observed localization of several enzymes to engineered compartments in *E. coli* using the expression cassette containing a constitutive $P_{lac}*$ promoter and $(GS)_6$ linker. In each case, co-expression of shell proteins EutS or EutSMNLK with the $EutC^{1-19}$-tagged cargo enzyme fused to EGFP led to fluorescent localization as seen before with $EutC^{1-19}$-EGFP. FIG. 20 shows, as one example, localization of a bacterial lipase (BTL-2) to EutS compartments in *E. coli*. Note that in the absence of EutS, BTL-2 (which is prone to aggregation) forms aggregates at the cell poles. Upon co-expression of EutS, the majority of the tagged lipase localizes to a compartment formed somewhat off-center in *E. coli*, consistent with prior observations

TABLE 1

Quantification of the distribution of recombinant Eut BMCs in *E. coli*.

I. Quantification of the ratio of cells with recombinant BMC by fluorescence microscopy

| E. coli strain | Gene combination | Total number of cells | Number of cells with green flourescent foci | % cells with green flourescent foci | Average number of green flourescent foci per cell |
|---|---|---|---|---|---|
| C2566 | EGFP | 867 | 0 | 0 | 0 |
| C2566 | $EutC^{1-19}$-EGFP | 881 | 4 | 0.4 | 0 |
| C2566 | EGFP + EutS | 876 | 4 | 0.5 | 0 |
| C2566 | $EutC^{1-19}$-EGFP + EutS | 1023 | 890 | 87 | 1.2 |
| C2566 | EGFP + EutMNLK | 834 | 1 | 0.1 | 0 |
| C2566 | $EutC^{1-19}$-EGFP + EutMNLK | 964 | 6 | 0.6 | 0 |
| C2566 | EGFP + EutSMNLK | 843 | 2 | 0.2 | 0 |
| C2566 | $EutC^{1-19}$-EGFP + EutSMNLK | 912 | 766 | 84 | 1.3 |
| C2566 | EGFP + EutS-G39V | 813 | 2 | 0.3 | 0 |
| C2566 | $EutC^{1-19}$-EGFP + EutS-G39V | 861 | 4 | 0.4 | 0 |
| JM109 | EGFP | 992 | 7 | 0.7 | 0 |
| JM109 | $EutC^{1-19}$-EGFP | 897 | 7 | 0.8 | 0 |
| JM109 | EGFP + EutS | 901 | 5 | 0.6 | 0 |
| JM109 | $EutC^{1-19}$-EGFP + EutS | 986 | 828 | 84 | 1.2 |
| JM109 | EGFP + EutMNLK | 931 | 7 | 0.8 | 0 |
| JM109 | $EutC^{1-19}$-EGFP + EutMNLK | 839 | 5 | 0.6 | 0 |
| JM109 | EGFP + EutSMNLK | 941 | 17 | 1.8 | 0 |
| JM109 | $EutC^{1-19}$-EGFP + EutSMNLK | 1011 | 799 | 79 | 1.1 |
| JM109 | EGFP + EutS-G39V | 821 | 24 | 2.9 | 0 |
| JM109 | $EutC^{1-19}$-EGFP + EutS-G39V | 886 | 71 | 8 | 0 |

II. Quantification of the ratio of *E. coli* (90 nm thin sections) with BMC structures by TEM

| E. coli strain | Gene combination | Total number of cells | Number of E. coli thin sections with BMCs | % of E. coli thin sections with BMCs |
|---|---|---|---|---|
| JM109 | EutS | 400 | 63 | 15.75 |
| JM109 | EutSMNLK | 270 | 60 | 22.22 |

Activity of Functional Enzymes Targeted to Engineered Compartments

To facilitate targeting of multiple, heterologous cargo enzymes into engineered nanocompartments, we developed expression cassettes based on our in-house BIOBRICK expression plasmids for convenient stacking and inducible ($P_{Bad}$ promoter) or constitutive ($P_{lac}*$) co-expression of cargo proteins (FIG. 20). In these constructs, cargo enzymes with $EutC^{1-19}$-EGFP. These results prove our ability to direct various different, unrelated cargo proteins to the interior of the compartments.

Figure 21:
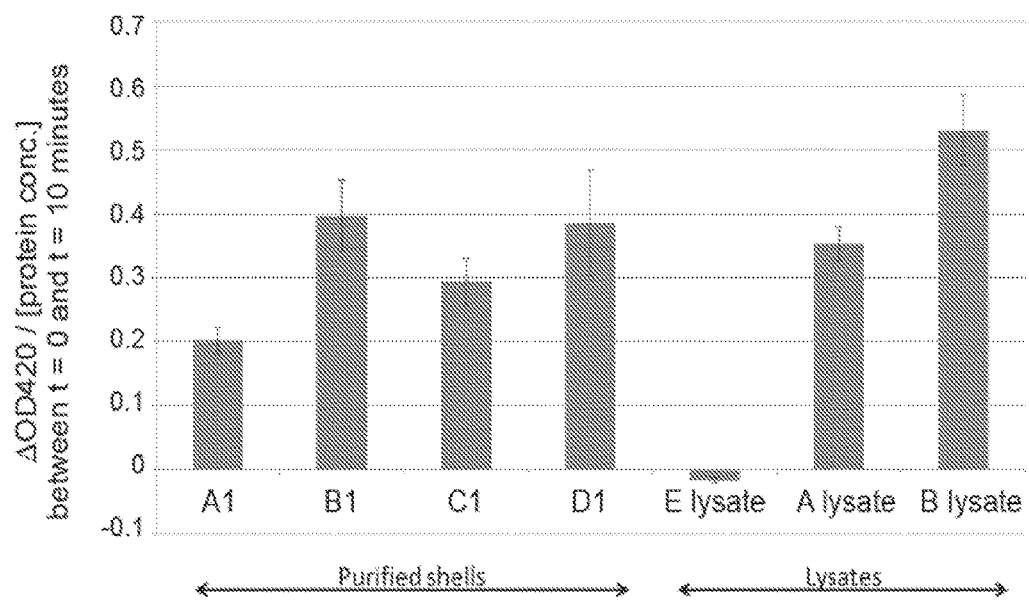
FIG. 21. in vitro BTL2 activity from isolated Eut microcompartments. Values represent the mean fold induction following 10 min of incubation of three biological replicates. X-axis labels are as follows: A, EutS+BTL2; B, EutS+EutC$^{1-19}$-BTL2; C, EutSMNLK+BTL2; D, EutSMNLK+EutC$^{1-19}$-BTL2; E, NHis-EutS only control.

To assess the activity of functional enzymes in vitro, His-tagged EutS was used as above to allow for rapid isolation of BTL2-expressing cells in conjunction with EutS or EutSMNLK BMC shells. The $EutC^{1-19}$ signal sequence was once again employed to target BTL2 to the interior of Eut BMCs as shown in FIG. 20. Following isolation, BTL2 activity was analyzed using a colorimetric, para-nitrophenyl (PNP)-palmitate assay (FIG. 21).

It is clear from these experiments that BTL2 can be co-isolated with EutS and EutSMNLK shells and that it remains biochemically active following isolation. These results provide proof-of-concept for the use of our BMC technology for the targeted expression of functional enzymes in BMCs not only in vivo, but also in vitro. This work therefore establishes a general platform from which one can engineer BMCs to include particular enzymes and carry out designed, targeted biochemistry.

Using the Eut BMC shell proteins from S. enterica as our model system, we demonstrate that proteinaceous subcellular compartments can be engineered in a heterologous host cell. We also show that heterologous proteins are efficiently targeted into the recombinant compartments, therefore enabling engineering of multi-step biocatalysis within tailored microcompartments as in vivo or in vitro nanobioreactors.

In this study, we made the surprising discovery that, in certain embodiments, only one model BMC shell proteins, EutS, can be necessary and sufficient for microcompartment formation within a model host cell. Recombinant EutS forms well-defined compartments that closely resemble the native Eut BMCs formed by S. enterica. Previously, the "bent" hexamer formed by wild type EutS in 3D crystals had led to the hypothesis that it forms the edges of the BMC shell (Tanaka et al. 2010 Science 327:81-84). Our data indicate that EutS also can form the facets of the capsid, raising the possibility that it adopts more than one conformation in vivo. Remarkably, in this embodiment, EutS also is necessary and sufficient for targeting EutC-signal sequence tagged model cargo proteins—EGFP and β-galactosidase—to the recombinant compartment. The EutS-G39V mutant, which forms flat symmetric hexamers (Tanaka et al. 2010 Science 327:81-84), is unable to sequester targeted EGFP, suggesting that the unusual bent configuration adopted by EutS in 3-D crystal lattices is physiologically relevant to the role played by EutS in this embodiment of the engineered microcompartment.

Another significant observation was the successful hydrolysis of X-gal by β-galactosidase localized to the EutS and EutSMNLK compartments, which indicates that these shells allow the indole galactopyranoside to pass through to the interior. Possible exemplary routes by which X-gal may gain access to the interior of shells include entry through central pores in shell protein multimers or via possible gaps between adjacent multimers that form the shell. Without wishing to be bound by any particular theory or mechanism, one possible route by which an enzyme substrate such as X-gal can access the interior of a BMC shell may be a large but occluded central pore that has been reported in the 3-D crystal structures of EutS and PduU, a close homolog of EutS (Tanaka et al. 2010 Science 327:81-84; Crowley et al. 2008 Structure 16:1324-1332). While a rearrangement of the protein may be involved in opening the central pore of EutS, such a rearrangement is not without precedent. For example, exposure to zinc ions can cause the central pore of EutL to adopt an "open" conformation (Takenoya et al. 2010 J Bacteriol 192:6056-6063). Additionally, two-dimensional (2-D) crystal studies of EutM revealed a tiling pattern with apparent gaps between adjacent hexamers, a phenomenon not observed in the 3-D crystal structure (Papapostolou and Howorka 2009 Mol Biosyst 5:723-732; Takenoya et al. 2010 J Bacteriol 192:6056-6063). This observation raises the possibility that EutS hexamers, and indeed other Eut BMC proteins, also can form 2-D lattices which are not as tightly packed as those observed in their 3-D crystals.

It is possible that the EutMNLK shell proteins may impart some level of selectivity toward the small molecules allowed to enter or exit the BMC shell. For example, EutL can crystallize as a pseudohexamer with a large, gated central pore that may be involved in transporting substrates and bulky cofactors into the shells while preventing the loss of reaction intermediates (Papapostolou and Howorka 2009 Mol Biosyst 5:723-732; Takenoya et al. 2010 J Bacteriol 192:6056-6063). Other possible roles of EutMNLK in the native S. enterica Eut BMCs include, for example, interactions with the encapsulated ethanolamine utilization enzymes, thereby regulating their spatial organization within the compartment (Yeates et al. 2011 Curr Opin Struct Biol 2011:21).

Heterologous reconstitution of Eut BMCs can provide an important tool for studying the functional roles of the EutMNLK proteins. While S. enterica cells can contain multiple Eut BMCs distributed throughout the cytoplasm, recombinant compartments in E. coli were typically limited to only one or two per cell. Some of the non-BMC-shell eut genes may be involved in the formation of more than one microcompartment per cell through, for instance, transcriptional regulation (Sheppard and Roth 1994 J Bacteriol 176:1287-1296). The off-center location of the recombinant microcompartments also was consistent. A recent report indicates that cyanobacterial carboxysomes are in motion within the cell and interact with the cytoskeleton, thereby ensuring their equitable distribution during cell division (Savage et al. 2010 Science 327:1258-1261). If one or more of the non-BMC-shell Eut proteins (for example EutP, an Era (E. coli Ras-like protein)-like GTPase) are required for interacting with the bacterial cytoskeleton, the intracellular location of the recombinant shells may simply result from aberrant interactions with the cytoskeleton, leading to altered nucleation of the microcompartment. Our observation that native Eut BMCs exhibit movement in S. enterica, while recombinant Eut shells appear to be stationary in E. coli, is consistent with this possibility.

Our results show that engineered BMC protein shells can be engineered to sequester heterologous enzymes for catalysis. An alternative approach for enzyme encapsulation involves adding oppositely charged amino acids to a non-BMC shell protein (lumazine synthase) and the encapsulated enzyme (Worsdorfer et al. 2011 Science 331:589-592), which involves optimizing electrostatic interactions between shell and cargo proteins while maintaining the catalytic efficiency of each sequestered enzyme. In contrast to this alternate approach, our in vivo system involving BMC protein shells and cargo protein-BMC targeting sequence fusions is much simpler and very specific.

Our data support the general feasibility of producing and exploiting cells that contain engineered compartments for sequestered catalysis. We have engineered model cells to produce compartments that include structural polypeptides of a model pathway and we show that these compartments can sequester a model enzyme targeted for the compartment. These results establish a general platform from which alternative embodiments of the model system may be designed.

For example, we employed structural polypeptides of the pathway for ethanolamine utilization (Eut). Other pathways that involve BMCs are known and may be employed. Exemplary alternative pathways include, for example, propanediol utilization (Pdu), ethanol utilization (Etu), or ribulose-1,5-bisphosphate (RuBP) metabolism.

As another example, we use Eut polypeptides from *Salmonella enterica*. However, many other microbial species are known to form BMCs including, for example, other members of the family Enterobacteriaceae such as, for example, members of the genus *Citrobacter*; members of the family Halothiobacillaceae such as for example, members of the genus *Halothiobacillus*; members of the domain Archaea such as, for example, members of the genus *Halobacteria* or members of the genus *Candidatus*; or members of the phylum Cyanobacteria such as, for example, members of the genus *Synechocystis*

Also, we used *E. coli* as a model host cell. Other exemplary host cells can include other gram-negative bacteria such as, for example, members of the family Shewanellaceae such as, for example, members of the genus *Shewanella*, members of the family Ralstoniaceae such as, for example, members of the genus *Ralstonia*, members of the family Pseudomonadaceae such as, for example, members of the genus *Pseudomonas*, or members of the family Bradyrhizobiaceae such as, for example, members of the genus *Bradyrhizobium*; gram-positive bacteria such as, for example, members of the family Bacillaceae such as, for example, members of the genus *Bacillus*, members of the family Streptomycetaceae such as, for example, members of the genus *Streptomyces*, or members of the family Corynebacteriaceae such as, for example, members of the genus *Corynebacterium*; yeast such as, for example, members of the family Saccharomycetaceae such as, for example, members of the genus *Saccharomyces* or members of the genus *Candida*, members of the family Dipodascaceae such as, for example, or members of the genus *Yarrowia*; members of the phylum Cyanobacteria such as, for example, members of the genus *Synechocystis* or members of the genus *Nostoc*.

Finally, we used targeted EGFP and targeted β-galactosidase as a model targeted cargo proteins. We further demonstrated that of the two model cargo proteins we tested, the enzymatic targeted cargo protein, β-galactosidase, retained enzymatic function after being targeted to the engineered BMC. Any suitable enzyme that catalyzes any desired reaction, however, can be engineered to include a compartment-specific signal sequence. Thus, it is possible to engineer cells to contain designed compartments that include one or more enzymes to catalyze any predetermined enzymatic reaction or predetermined sequence of reactions. For example, one can design multi-enzyme pathways; sequestration of pathway intermediates can increase the efficiency of such pathways compared to similar pathways in other environments.

Figure 17:
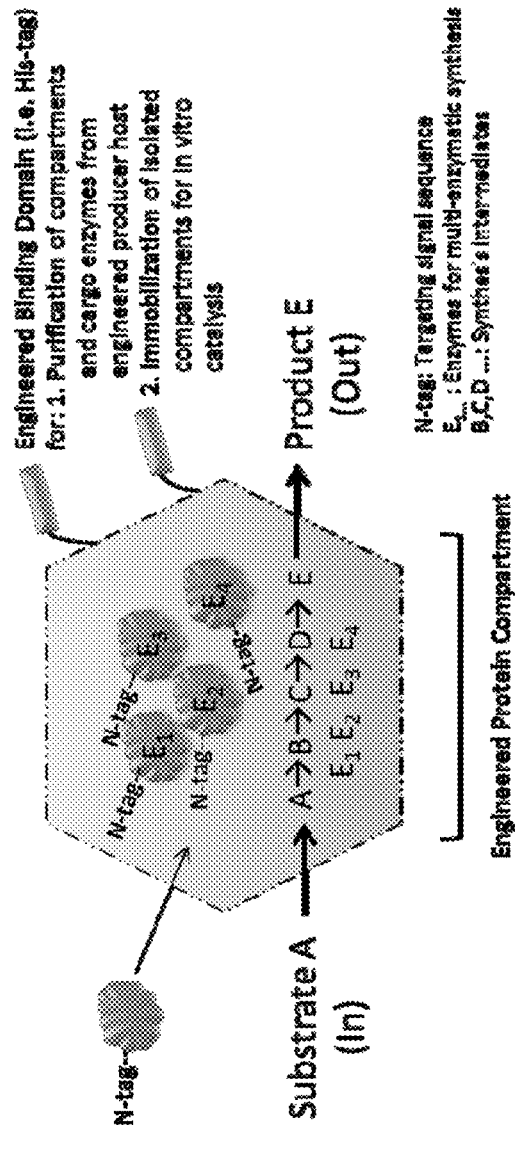
FIG. 17. Schematic representation of multi-enzymatic synthesis in engineered protein compartments (A). Examples for co-factor recycling systems, which may be co-localized with compartmentalized enzymes if needed, are also shown (B).
Figure 17:
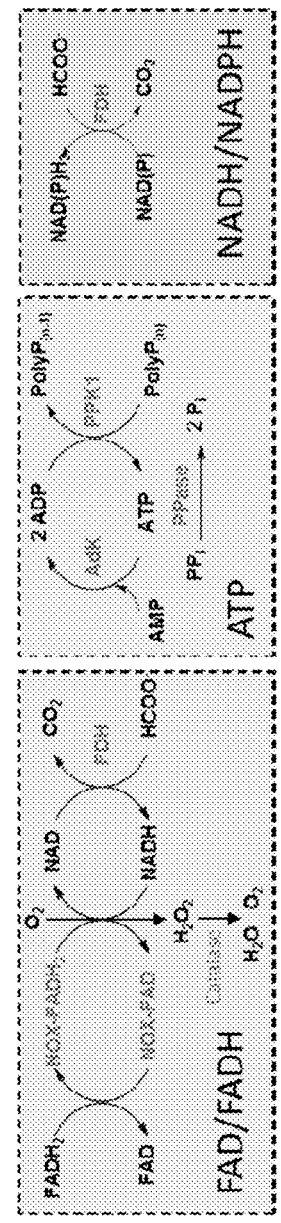

Table 2 identifies exemplary applications in which catalytic pathways can be reconstituted in compartments either for use in a heterologous production host or in vitro biocatalysis. In the latter case, one or more additional heterologous enzymes may be introduced into the cell such as, for example, by transformation. The heterologous enzyme may be targeted to the compartment to provide for necessary co-factor recycling, catalytic amounts of co-factors and, in some cases such as Application 1, a substrate that is not otherwise provided by host (extra components/substrates underlined). Co-factor recycling modules are schematically described in FIG. 17.

TABLE 2

| Exemplary pathways for targeting into protein compartments. | | |
|---|---|---|
| Substrate | Enzymes in Compartment | Product |
| Application 1: Bioactive plant natural products Flavored/stilbenes (in vivo/in vitro production) | | |
| Malonic acid, tyrosine Catalytic of coenzyme A, ATP, polyphosphate for co-factor recycling | 1. Tyrosine ammonia lyase (i.e. *Rhodobacter sphaeoides*) 2. 4-coumaryl-CoA ligase (i.e. *Arabidopsis thaliana*) 3. Chalcone synthase (flavonoids) (i.e. *A. thaliana*) 4. Stilbene synthase (stilbenes) (*Medicago truncatula*) 5. ATP recycling module enzymes | Flavonoid Stilbene |
| Application 2: Bioactive polyketide drug Erythromycin (6dEB) (in vivo/in vitro production) | | |
| Propionate Catalytic amounts of biotin (for PCC), coenzyme A, ATP, polyphosphate for co-factor recycling | 1. PKS modules DEBS1, DEBS2, DEBS 2 from *Saccharopolyspora erythraea* 2. PrpE propionyl-CoA synthase (i.e. *Salmonella typhimurium* LT2) 3. Propionyl-CoA carboxylase (PCCA, PCCB subunits) (i.e. *Streptomyces coelicolor* (additonal enzymes as needed to derivatize core scaffold) 4. ATP recycling module enzymes | 6-deoxyerythronolide B (6dEB) (minimal core scaffold of erythromycins) |
| Application 3: Biofuel | | |

TABLE 2-continued

Exemplary pathways for targeting into protein compartments.

| Substrate | Enzymes in Compartment | Product |
|---|---|---|
| Isobutanol (in vivo production) | | |
| Pyruvate [NADPH$_2$ + NADH] *Sugar carbon source converted by host to pyruvate | 1. Acetolactate synthase (AlsS, bacillus subtilis) 2. Acetohydroxy acid isomeroreductase (IlvC, E. coli) 3. Dihydroxy acid dehydratase (IlvD, E. coli) 4. 2-ketoacid decarboxylase (Kivd, Lactococcus lactis) 5. Alcohol dehydrogenase (Adh2, S. cerevisiae) | Isobutanol [NADP$^+$ + NAD$^+$] |
| Application 4: Degradation Furfural/furane detoxification for biofuel production by biofuel production host (in vivo application) | | |
| Furane (i.e. hydroxyl-methyl furfural (HMF) or furfuryl alcohol) [NAD$^+$] | 1. GMC oxidoreductase (HmfH Cupriavidus basiliensis) 2. Dicarboxylic acid decarboxylase (HmfGH, C. basiliensis) 3. Catalase (E. coli) to cleave harmful H$_2$O$_2$ generated in degradation process | Non-toxic 2-furoic acid (may be further degraded to TCA intermediate 2-oxo-glutarate by HmfD, HmfABC, HmfE from C. basiliensis) |
| Application 5: Rosmarinic Acid | | |
| hydroxyphenylpyruvate (HPP) | 1. hdhA 2. hpaBC | 3,4-DHPL in compartment may undergo further biosynthesis to rosmarinic acid |

Figure 22:
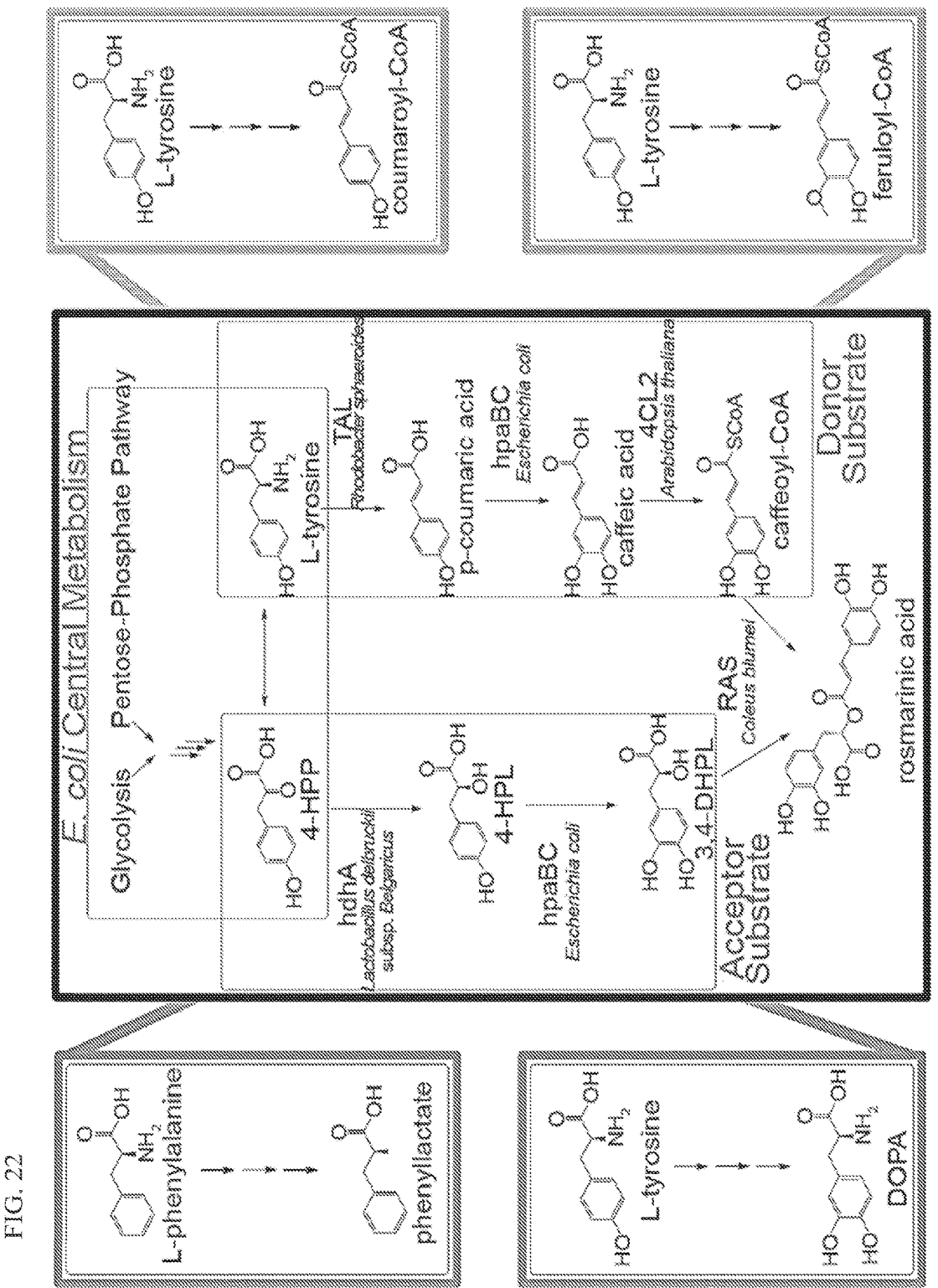
FIG. 22. Heterologous expression of Eut BMC constructs in *S. cerevisiae*. Representative DIC and epifluorescent images are shown for all relevant constructs following induction with galactose.

For example, Application 5 in Table 2 reflects the use of BMCs for producing the hydroxycinnamate ester rosmarinic acid. Rosmarinic acid is an antioxidant found in many culinary herbs and is used as a natural food preservative. It is also a GABA-transaminase inhibitor, giving it potential as a drug in the treatment of anxiety and related disorders. In plants, the rosmarinic acid biosynthetic pathway requires ten enzymatic steps, including catalysis by cytochrome P450s, which can be problematic in industrial microbes. By using bacterial enzymes shown to have the same or similar activities to the plant enzymes, we have designed a novel route to rosmarinic acid biosynthesis in Escherichia coli requiring only six enzymes, four of which are bacterial in origin. (FIG. 22). This engineered biosynthetic pathway for rosmarinic acid (RA) biosynthesis in E. coli includes two precursor pathways: one to produce the donor substrate 3,4-dihydroxyphenyllactate (3,4-DHPL) and a second to produce the acceptor substrate caffeoyl-CoA. Finally, the formation of the ester linkage between the two substrates is catalyzed by rosmarinic acid synthase (RAS) (FIG. 22).

In order to produce rosmarinic acid through fermentation, caffeoyl-CoA and 3,4-DHPL should occur simultaneously in the same cell. Using the same hpaBC enzyme complex for both caffeoyl-CoA and 3,4-DHPL biosynthesis in the same cellular compartment—e.g., the cytoplasm—can be problematic, however, as hpaBC seems to have a much higher affinity for coumarate (p-coumaric acid in FIG. 22) than for 4-HPL, thus favoring production of one precursor at the expense of producing the other required precursor.

Sequestering the biosynthetic pathways using bacterial microcompartments, however, can overcome this problem. For example, hdhA and hpaBC may be localized into a BMC. The precursor hydroxyphenylpyruvate (HPP) can diffuse into the BMC and be converted to 4-HPL by hdhA. The BMC shell will then limit the diffusion of 4-HPL sufficiently to increase its local concentration with respect to the BMC-localized hpaBC, increasing the velocity of hpaBC-catalyzed conversion of 4-HPL to 3,4-DHPL, which will accumulate in the BMC since the BMC contains no further enzyme for catalysis or biosynthesis involving 3,4-DHPL. Accumulation of 3,4-DHPL in the BMC will drive diffusion of 3,4-DHPL out of the BMC and into the cytoplasm.

Meanwhile, a second copy of the hpaBC enzyme can be expressed outside the BMC to catalyze caffeoyl-CoA biosynthesis.

As shown in FIG. 22, rosmarinic acid synthase in the cytoplasm catalyzes the linking of the caffeoyl-CoA, synthesized via the cytoplasmic hpaBC, and the 3,4-DHPL, synthesized via the BMC-localized hpaBC to form rosmarinic acid.

Rapid Isolation of Nanocompartments with Encapsulated Cargo Proteins

In some cases, the compartments may be designed to include a tag to assist with harvesting compartments and the catalytic products contained in the compartments. In some cases, the compartments may be harvested by breaking open the cells and contacting a sample that includes the tagged compartments with a substrate having a complement to the tag. Exemplary tags include, for example, a histidine tag, but other affinity-based tags are also possible such as, for example, a GST-tag, a MBP-tag, a CBP-tag, a FLAG-tag, a CYD-tag, an HPC-tag, a Strep-Tag, a Poly-Lysine/Arginine tag, or a Poly-Glutamate/Aspartate-tag.

To facilitate rapid isolation of compartments with their encapsulated cargo enzymes, we have engineered a EutS shell protein that carries an N-terminal 6× Histidine tag. Co-expression of 6×His-EutS (from a low-copy number pBBR-plasmid) with untagged EutS or EutSMNLK (from a high-copy number pUC-plasmid) enables one-step isolation of compartments (FIG. 19A) from lysed E. coli cells by metal-affinity chromatography with magnetic beads (Millipore; Billerica, Mass.). We also demonstrated that recombinant EutC$^{1-19}$-β-galactosidase (expressed from a pACYC-plasmid) co-isolated with the compartments (FIG. 19B, EutS compartments shown) and is catalytically active; the encapsulated enzyme hydrolyzed ortho-nitrophenol-β-galactoside, confirming substrate and product exchange across shells which we previously demonstrated for compartments inside E. coli cells. TEM analysis (FIG. 19C) of the affinity-isolated compartments showed that their morphology resembles compartments previously isolated by sucrose gradient ultracentrifugation from recombinant E. coli cells. 2D-gel electrophoresis (FIG. 19D) of EutSMNLK compartments with sequestered β-galactosidase indicate EutS, EutM and EutN as the most abundant, and EutL and EutK as the least abundant, shell proteins in the isolated compartments.

In the preceding description, particular embodiments may be described in isolation for clarity. Unless otherwise expressly specified that the features of a particular embodiment are incompatible with the features of another embodiment, certain embodiments can include a combination of compatible features described herein in connection with one or more embodiments.

For any method disclosed herein that includes discrete steps, the steps may be conducted in any feasible order. And, as appropriate, any combination of two or more steps may be conducted simultaneously.

The present invention is illustrated by the following examples. It is to be understood that the particular examples, materials, amounts, and procedures are to be interpreted broadly in accordance with the scope and spirit of the invention as set forth herein.

EXAMPLES

Microbiological Methods.

E. coli strains JM109 and the BL21 derivative C2566 were obtained from Sigma and New England Biolabs, respectively. Salmonella enterica serovar Typhimurium LT2 was a kind gift from Dr. Jeffrey A. Gralnick (University of Minnesota).

E. coli cultures were cultivated aerobically at 30° C. for 15-18 hours in Luria-Bertani (LB) medium supplemented with the appropriate antibiotic when required (ampicillin 100 μg/ml, chloramphenicol 50 μg/ml). For the in vivo β-galactosidase assay, cultures were grown overnight with X-gal (final concentration: 0.008% (w/v)). S. enterica cultures were grown aerobically at 37° C. overnight in supplemented E medium with 150 nM vitamin $B_{12}$ (cyanocobalamin) and either 0.2% (v/v) glycerol or 30 mM ethanolamine (Brinsmade et al. 2005 J Bacteriol 187:8039-8046). 30 μg/ml kanamycin was added to the growth media for culturing S. enterica strains containing pBBRBB-based plasmids.

General Molecular Biology Methods.

Illustra GFX PCR DNA and gel band isolation kit (GE Healthcare; Niskayuna, N.Y.) was used for all agarose gel and PCR isolations. Plasmid DNA was isolated using Promega Wizard Plus SV Minipreps DNA Isolation kit according to the manufacturer's instructions. Restriction enzymes and T4 DNA ligase were obtained from New England Biolabs (Ipswich, Mass.) and Invitrogen (Grand Island, N.Y.), respectively. Standard protocols were used for restriction digests and DNA ligation (Webster 2007 Methods Mol Biol 369:47-65).

BIOBRICK-Based Expression Vectors.

Figure 8:
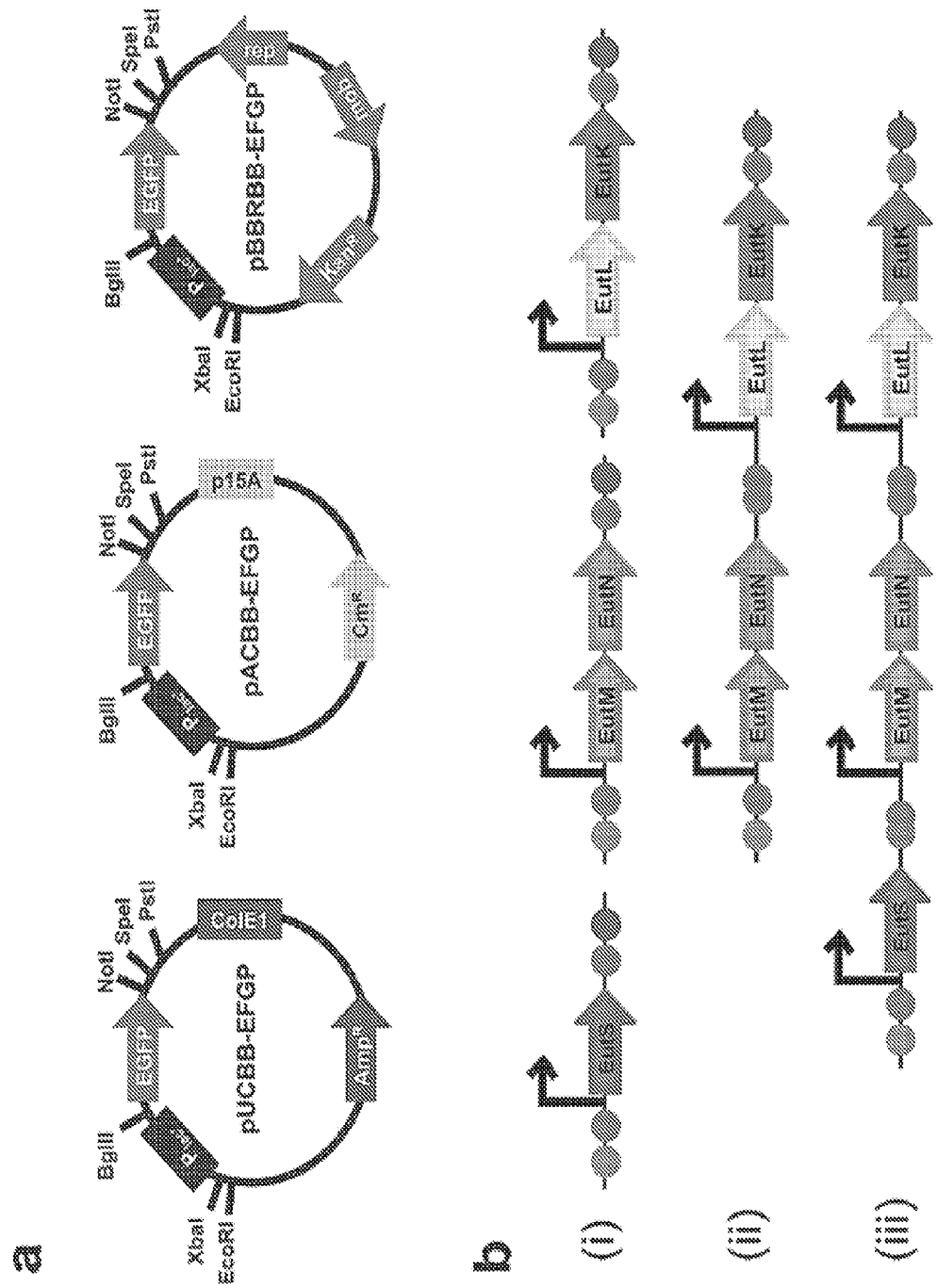
FIG. 8. Vectors and strategy for stacking multiple genes into a single plasmid. (a) Diagrams of vectors containing an expression cassette with a constitutive promoter ($P_{lac}$*) and an EGFP reporter. (b) Cloning of Eut BMC shell genes into pUCBB. (i) EutS, EutMN and EutLK were cloned downstream of the constitutive $P_{lac}$* promoter (black arrow) using BglII and NotI. (ii) and (iii) Expression cassettes for EutMNLK and EutSMNLK were created as described in Supplementary Methods.
Figure 9:
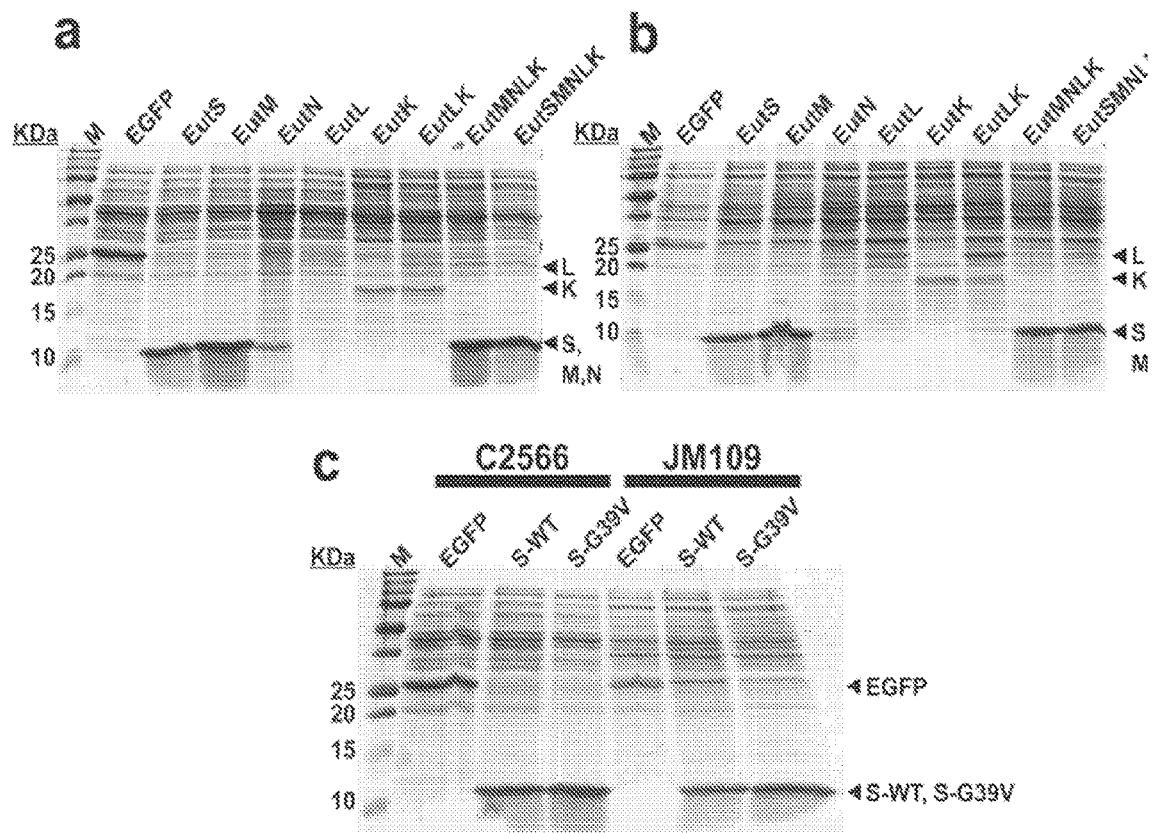
FIG. 9. SDS/PAGE analysis showing recombinant expression of *S. enterica* Eut shell proteins in *E. coli*. (a) Overexpression of Eut shell proteins in the *E. coli* strain C2566. (b) Overexpression of Eut shell proteins in the *E. coli* strain JM109. (c) Overexpression of wild type EutS and the EutS-G39V mutant in *E. coli* strains C2566 and JM109. 15 μg soluble protein fraction was loaded in each lane. Expected protein sizes are as follows: EutS (11.6 kDa), EutM (9.8 kDa), EutN (10.4 kDa), EutL (22.7 kDa), EutK (17.5 kDa), and EGFP (26.9 kDa). Proteins were stained with Coomassie Blue.

The BIOBRICK strategy allows for rapid sub-cloning of genes into several vectors using the same set of restriction enzymes (FIG. 8). Our BIOBRICK-based expression vectors have a constitutively active modified lac promoter ($P_{lac}$*) (Savage et al. 2010 Science 327:1258-1261). Various open reading frames can be inserted between the BglII and NotI sites downstream of $P_{lac}$*. pUCBB (ampicillin resistance) and pACBB (chloramphenicol resistance) have ColE1 and p15A origins of replication, respectively, while pBBRBB (kanamycin resistance) is derived from the broad-host-range vector pBBR1MCS (Dunwell et al. 2004 Phytochemistry 65:7-17).

Gene Cloning.

Eut shell genes were amplified from S. enterica LT2 genomic DNA (ATCC catalog number 700720D-5) with gene specific primers containing suitable restriction sites. Their accession numbers are as follows: EutS (NP_461405), EutM (NP_461400), EutN (NP_461399), EutL (NP_461391), and EutK (NP_461390). Restriction sites for BglII and NotI were added to the 5' end of the forward and reverse primers, respectively. Each PCR product was gel isolated and digested with BglII and NotI, followed by ligation with BglII/NotI digested pUCBB. All cloned sequences were confirmed by DNA sequencing. The eut genes were cloned into expression vector pUCBB, and expressed from a constitutively active modified lac promoter as described previously (FIG. 8) (Schmidt-Dannert et al. 2000 Nat Biotechnol 18:750-753).

The expression cassettes were stacked sequentially to produce the vectors pUCBBEutMNLK and pUCBBEutSMNLK. To stack the Eut expression cassettes, pUCBBEutMN and pUCBBEutLK were digested with EcoRI/SpeI and EcoRI/XbaI respectively. XbaI and SpeI produce compatible DNA ends that upon ligation generate a "scar" which cannot be recognized by either enzyme. The $P_{lac}$*-EutMN DNA fragment was ligated into digested pUCBBEutLK to produce the vector pUCBBEutMNLK. Next, pUCBBEutS was digested with EcoRI/SpeI, and the $P_{lac}$*-EutS fragment ligated into EcoRI/XbaI digested pUCBBEutMNLK to produce the final vector pUCBBEutSMNLK. EutM, EutN, EutL and EutK were also cloned singly to study their individual contributions to BMC formation. For expression in S. enterica, EGFP, EutC$^{1-19}$-EGFP and EutG$^{1-19}$-EGFP were further sub-cloned into our in-house broad-host-range BIOBRICK-based expression vector pBBRBB.

The EutS-G39V mutant was created by site-directed mutagenesis.

β-galactosidase (amplified from E. coli MG1655 genomic DNA) and EGFP were cloned into the low copy number BIOBRICK-based expression vector pACBB. Nucleotides coding for the putative EutC-signal sequence (EutC$^{1-19}$) from S. enterica LT2 (MDQKQTEEIVRSVMASMGQ, SEQ ID NO:1) were added to N-terminus of EGFP and β-galactosidase through PCR (Fan et al. 2010 Proc Natl Acad Sci USA 107:7509-7514). Similarly, EGFP was also tagged with the predicted EutG-signal sequence (EutG$^{1-19}$) from E. coli K12 (MQNELQTALFQAFDTLNLQ, SEQ ID NO:2), which differs from the S. enterica LT2 EutG$^{1-19}$ by one amino acid. Both putative signal sequences were codon optimized for expression in *E. coli*.

Transmission Electron Microscopy (TEM).

Bacterial cells were fixed in 2.5% glutaraldehyde in 0.1 M phosphate buffer, followed by three washes with 0.1 M phosphate buffer. Triton X-100 was added to the glutaraldehyde solution and rinse buffer to a final concentration of 0.1%. Subsequently, the pellets were post-fixed with 1% osmium tetroxide in 0.1 M phosphate buffer, washed with nanopure water, and embedded in 2% low melting agarose. The cell-agarose pellet was cut into 1 mm$^3$ cubes, and dehydrated using an ethanol gradient. The cell-agarose cubes were then incubated in 1:1 mixture of Embed 812 resin and 100% ethanol for four hours, followed by an 18-hour incubation in 100% Embed 812 resin. Next, they were suspended in a fresh Embed 812 resin-N,N-dimethylbenzylamine (BDMA) solution and polymerized at 60° C. for 48 hours. 90 nm sections were sliced, placed on 200 mesh formvar-coated copper grids, and post-stained with 3% uranyl acetate and Triple lead stain. Specimens were observed and photographed with a Philips CM12 transmission electron microscope.

Light Microscopy.

Bacteria were viewed using a Nikon Eclipse E800 photomicroscope equipped with bright field, Differential Interference Contrast (DIC) and fluorescence optics including blue (excitation filter 470-490 nm, bather 520-580 nm) and green (excitation filter 510-560 nm, barrier 570-620 nm) filter sets. The samples were viewed using a 100×, 1.4 n.a. plan apo objective. For fluorescence microscopy, 16-bit digital images were collected using a Roper CoolSnap HQ monochrome camera and captured using Image Pro Plus software. DIC microscopy was performed using a 1.4 n.a. oil condenser. Z-series images of cells were collected at 0.15 micron steps using a Ludl MAC 3000 controller interfaced with ImagePro Plus. The DIC images were deconvolved using the SharpStack Nearest Neighbor algorithm. A minimum projection of the resulting z-series was made and all images were identically adjusted for display using PhotoShop.

Isolation of BMCs.

*S. enterica* cells were made electrocompetent, and were transformed with pACBBEutC$^{1-19}$-EGFP. Cells harboring the plasmid were grown in one liter of NCE minimal medium supplemented with 50 µg/ml chloramphenicol and 30 mM ethanolamine to induce Eut BMC production (Vogel and Bonner 1956 J Biol Chem 218:97-106). *E. coli* C2566 cells harboring pUCBBEutSMNLK or pUCBBEutS also were transformed with pACBBEutC$^{1-19}$-EGFP and were grown in one liter of LB medium supplemented with 100 ampicillin and 50 µg/ml chloramphenicol. *E. coli* C2566 cells harboring pACBBEutC$^{1-19}$-EGFP also were grown as a control. Cultures were grown at 37° C. with shaking at 275 rpm for 16 hours. Cells were harvested by centrifugation at 10,000×g for 30 minutes at 4° C.

Isolation of Eut BMCs was carried out using procedures previously described for Pdu BMCs, with the exception that the TEMP buffer was replaced by a TEME buffer (50 mM Tris.HCl, 10 mM MgCl$_2$, 2 mM EDTA, 30 mM ethanolamine (pH 8.0)), and that the BMCs were applied to two separate discontinuous sucrose gradients: firstly, a three step gradient of 20%, 40%, and 65% sucrose, and secondly a ten step gradient from 22% to 54% sucrose (Havemann and Bobik 2003 J Bacteriol 185:5086-5095). Native Eut BMCs from *S. enterica* harboring EutC$^{1-19}$-EGFP and recombinant EutSMNLK and EutS BMCs from *E. coli* harboring EutC$^{1-19}$-EGFP formed a white translucent band two thirds the way down the centrifuge tube, which was also checked for fluorescence under UV light due to the localization of EutC$^{1-19}$-EGFP into the BMCs. Following a final clarification step, the native Eut BMCs and recombinant EutSMNLK and EutS shells were pelleted, and sample purity was judged to be sufficient for TEM by SDS-PAGE electrophoresis. Isolated BMC samples were fixed and negatively stained according to previously published procedures, with the exception that 2% uranyl acetate was used for staining (Havemann and Bobik 2003 J Bacteriol 185:5086-5095). The isolation and negative staining procedures were repeated on separate occasions to ensure consistency in results and reproducibility of the procedure.

Anti-GFP Immunogold Labeling and TEM.

Microwave-assisted low temperature processing was used to prepare *E. coli* cells for anti-GFP immunofluorescence and immunogold labeling. Steps for primary fixation of the samples were adapted from procedures published previously (Munoz et al. 2004 J Neurosci Methods 137:133-139; Webster 2007 Methods Mol Biol 369:47-65).

After microwave processing, the cell pellets were pre-embedded in 2% NuSieve agarose (Cambrex Life Sciences; East Rutherford, N.J.), and washed twice for 30 minutes each in phosphate buffer at 4° C. Dehydration substitution procedures were conducted in a block of dry ice with 1.5 ml microfuge tubes placed in 100% solvent filled pre-drilled holes. Samples were dehydrated/substituted in 50%, 75% and 96% Methanol, 1:1 96% Methanol: LR White resin, 100% LR White sequentially at dry ice temperatures in the presence of microwaves with the following wattages and times: 150 watts for 12 minutes (5 minutes on, 2 minutes off, 5 minutes on) each. The LR White infiltrated samples where then embedded with fresh LR White resin followed by polymerization at 42° C. for 18 hours. The polymerized blocks were sectioned (90 nm) with diamond knives and placed on formvar-coated nickel 200 mesh grids.

For immunogold labeling, sections were labeled for anti-GFP (Invitrogen; Grand Island, N.Y., Cat# A11122) using the indirect immunogold labeling technique. Grids with sections were floated on drops of blocking buffer, consisting of PBS, pH 7.2, with 5% normal goat serum, 1% glycerol, 0.1% bovine serum albumin (Fraction V; Sigma-Aldrich; St. Louis, Mo.), 1% fish skin gelatin, and 0.04% sodium azide for 15 minutes at room temperature (RT). Specimens were reacted overnight at 4° C. with the anti GFP antibody diluted 1:50. After washing seven times in droplets of PBS, the sections were incubated with 20 nm goat anti-rabbit IgG (1:50 dilution, GE Healthcare; Niskayuna, N.Y.). After washing seven times with droplets of PBS, the sections were fixed in 1% glutaraldehyde followed by rinsing on a droplet of water eight times. All sections were stained for 5 minutes with uranyl acetate and five minutes with lead citrate before observation on a Phillips CM 12 TEM.

Protein Analysis.

*E. coli* C2566 cells were grown at 37° C. for SDS/PAGE analysis of recombinant Eut protein expression, which was performed using standard methods (Webster 2007 Methods Mol Biol 369:47-65). Total cellular protein was extracted from pelleted overnight cultures using BugBuster (Novagen) extraction reagent. The extracts were centrifuged (12,000 rpm, 15 minutes, 4° C.) to separate the soluble and insoluble fractions. Protein concentrations were determined using Bio-Rad protein assay reagent (Bio-Rad; Hercules, Calif.). For studying expression of recombinant Eut proteins, PAGE was performed using 15% SDS gels and Bio-Rad Mini-Protean II electrophoresis cells as per the manufacturer's instructions. The protein gels were subsequently stained with Bio-Safe Coomassie Blue (Bio-Rad; Hercules, Calif.). Silver staining was used to visualize isolated Eut BMC proteins.

Western Detection of EutC$^{1-19}$-EGFP from Isolated BMCs.

Isolated native Eut BMCs and recombinant EutSMNLK and EutS shells harboring EutC$^{1-19}$-EGFP were broken by sonication. 10 μg of broken and intact compartments were loaded in separate lanes of a gel. Proteins were transferred to a PVDF membrane (Roche; Madison, Wis.), and were detected by a primary anti-GFP antibody from mouse and a secondary anti-mouse conjugated antibody (Invitrogen; Grand Island, N.Y.). A chromogenic developing solution was prepared using a one:one ratio of luminol/enhancer solution and stable peroxide solution (Thermo Scientific; Waltham, Mass.), and was applied to the membrane. The membrane was placed in a film cassette and was exposed to film (Bioexpress; Kaysville, Utah) for two minutes, and the film was subsequently developed.

Anti-GFP Immunofluorescence Studies.

*E. coli* cells were suspended in PBS for microwave-assisted low temperature processing. Microwave-assisted low temperature processing was conducted in a Pella Biowave Pro microwave processor equipped with a COLD-SPOT load cooler, vacuum system, and variable wattage. Bacterial pellets were initially fixed using 0.1% glutaraldehyde, 4% paraformaldehyde, and 0.1 M sodium phosphate buffer (pH 7.2), in the microwave processor at 150 watts for 12 minutes (5 minutes on, 2 minutes off, 5 minutes on) at 4° C. Subsequently, the cells were mounted on 10-welled microscope slides, permeabilized in −20° C. methanol for 10 minutes, and allowed to air dry. Drops of blocking buffer (PBS (pH 7.2) with 5% normal goat serum, 1% glycerol, 0.1% BSA, 1% fish skin gelatin, and 0.04% sodium azide) were placed on the attached cells for 15 minutes at room temperature. Specimens were reacted overnight at 4° C. with the anti-GFP antibody diluted 1:50 (Invitrogen; Grand Island, N.Y., Catalog no. A11122) and then incubated with Alexa 568 goat anti-rabbit IgG for two hours at 37° C. Finally, the cells were washed and mounted in Prolong Gold with DAPI. Preparations were viewed using the E800 microscope.

Nile Red Assay

Overnight cultures of bacteria were incubated with Nile Red (final concentration 1 ng/ml) for five minutes in the dark. Fluorescence visualization was performed using the Nikon E800 microscope as described.

HIS-Tag BMC Isolation

The EutK protein has an N-terminal BMC-type domain, which is followed by a 60 amino acid protein domain that appears to contain a helix-turn-helix motif commonly found in proteins that bind nucleic acids. A EutK mutant has been developed in which this extra domain has been deleted, and a C-terminal hexa-Histidine tag has been added (named EutK-BMC-His). This EutK mutant has been combined with EutS and EutSMNL to create a construct that produces recombinant shells containing His-tagged EutK.

These constructs are co-transformed with a plasmid expressing EutC$^{1-19}$-EGFP into *E. coli* JM109 cells. A single colony is picked up and inoculated in 4 mL LB (30° C. overnight). The 4 ml overnight culture is used to inoculate 500 ml LB (30° C. overnight). Cells are pelleted (4,000 rpm, 4° C., 20 minutes), washed once with 10 mL 1×TAE buffer (4,000 rpm, 4° C., 20 minutes), and then re-suspended in 10 ml BugBuster (Novagen, EMD Millipore, Billerica, Mass.) extraction reagent. The lysed cells are centrifuged (10,000 rpm, 4° C., 20 minutes) to separate the cell debris from the soluble fraction. 5 ml of the soluble fraction is loaded onto a Nickel Sepharose FPLC column (HisTrap HP, 5-ml column, GE Healthcare; Niskayuna, N.Y.).

Isolation of his-Tagged Eut Shells Using Magnetic Beads

His-tagged EutS was expressed from a lower copy plasmid (pBBRBB-NHis-EutS) using the constitutive $P_{lac}$* promoter. Expression from a lower copy plasmid was expected to decrease the ratio of tagged EutS with respect to untagged EutS (or EutSMNLK) in the shells, thereby reducing the harmful effects, if any, on the shell structure due to the presence of a tagged EutS.

*E. coli* C2566 cells harboring pBBRBB-NHis-EutS were co-transformed with pUCBB EutS, and the cargo protein was provided by pACBB EutC$^{1-19}$β-galactosidase. 10 ml overnight cultures were used to inoculate 500 ml LB cultures, which were grown at 30° C. for 15-18 hours. The culture pellets were washed with 100 ml Buffer 1 (50 mM Tris-HCl, pH 8, 0.6 M sucrose, 5 mM EDTA), then resuspended in 12.5 ml Lysozyme buffer (2 mg/ml lysozyme in Buffer 1). After a 10 minute incubation on ice, the samples were centrifuged at 4000 rpm for 20 minutes, and the supernatant was discarded. The pellets were washed with 25 ml Buffer 1, and then resuspended in sonication buffer (50 mM Tris-HCl, pH 8, 2 mM EDTA, using 0.1 g cell weight per ml sonication buffer.). The cells were sonicated (11% amplitude, 2 minutes total, 20 seconds ON, 40 seconds OFF), followed by incubation with DNAse at 37° C. for one hour. The cell debris was removed by centrifugation at 4000 rpm for 20 minutes. 15 ml cell lysate was incubated with 250 μl. PureProteome Nickel magnetic beads (EMD Millipore, Billerica, Mass.) at room temperature for 30 minutes, with gentle rotation. The magnetic beads were collected using a magnet, and were washed three times with 1 ml wash buffer (50 mM Tris-HCl, pH 8, 2 mM EDTA, 10 mM Imidazole, pH 8.0). Finally, the His-tagged shells were eluted in 200 μl elution buffer (50 mM Tris-HCl, pH 8, 2 mM EDTA, 300 mM imidazole, pH 8.0), and stored at 4° C.

Figure 19:
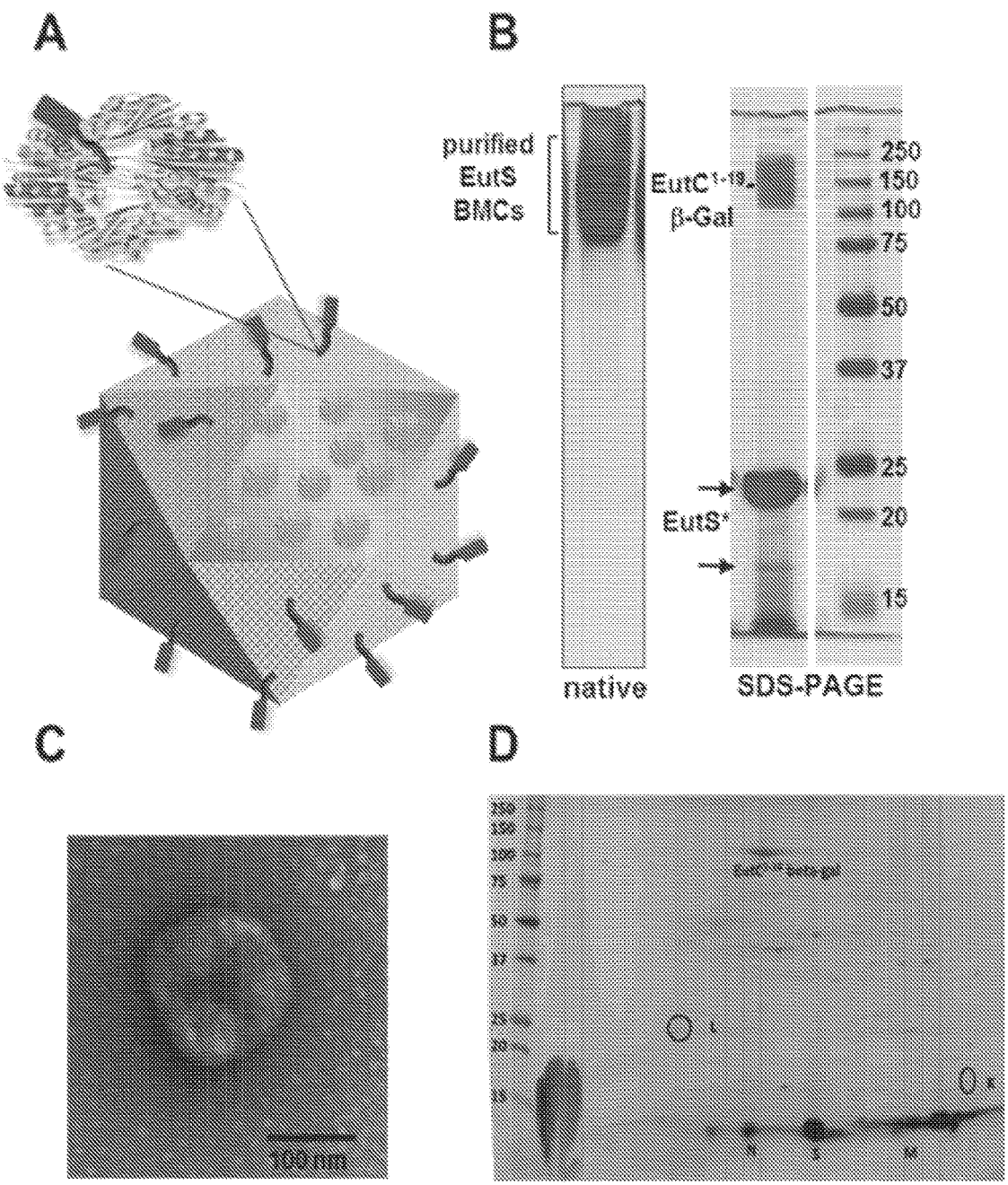
FIG. 19. One-step metal-affinity isolation of recombinant nanocompartments from *E. coli*. (A) Illustration of externally His-tagged compartments by co-expressing in *E. coli* both wild-type and N-terminally 6×His-tagged EutS (at a lower rate to avoid potential interference with compartment assembly and pore blockage). (B) PAGE-analysis of isolated compartments. Shown are representative images as examples of: native PAGE of EutS and SDS PAGE of EutSMNLK compartments with EutC$^{1-19}$-β-galactosidase cargo. Note that intact EutS compartments hardly migrate in the native PAGE gel. (C) TEM image of affinity isolated EutS shell. (D) 2D-gel electrophoreses of isolated EutSMNLK compartments with EutC$^{1-19}$β-galactosidase cargo.

5 μg of the isolated shells (with EutC$^{1-19}$-β-galactosidase cargo) were run on native PAGE and denatured SDS-PAGE gels. Results are shown in FIG. 19B.

The isolated shells were observed by negative stain TEM as described above, and their size and shape are comparable to the shells observed in vivo. Results are shown in FIG. 19C.

A similar protocol was used to purify EutSMNLK shells from *E. coli* C2566 cells harboring pBBRBB NHis-EutS and pACBB EutC$^{1-19}$-β-galactosidase. The isolated shells were resuspended in elution buffer 2 (7 M Urea, 2 M thiourea, 4% CHAPS, 1% dodecyl-beta-D-maltoside), and separated via 2-D electrophoresis. Bands corresponding to EutC$^{1-19}$β-galactosidase and the various shell proteins were visible, suggesting that the strategy employed here is capable of purifying recombinant Eut shells and the encapsulated cargo. Results are shown in FIG. 19D.

Intracellular Distribution of BMC-Tagged Cargo Proteins

For visualizing the intracellular distribution of various EutC$^{1-19}$-tagged cargo proteins, we created a modular expression cassette for producing signal sequence-tagged cargo proteins with a C-terminal EGFP fusion. Repeats of glycine-serine (GS) separate the signal sequence, cargo protein, and EGFP, in order to reduce possible steric hindrance to proper folding. Restriction sites (RE) are included for cloning the cargo protein in frame with the signal sequence and EGFP.

BTL2 lipase from *Bacillus thermocatelunatus* was cloned into this modular cassette, and its intracellular localization visualized using the methods described above. The basal cassette is regulated by the strong, constitutive $P_{lac}$* promoter and flexible GS linkers between the signal sequence and cargo protein and/or between the cargo protein and EGFP. In addition, cassettes have been built which are regulated by the inducible $P_{BAD}$ promoter, or contain rigid EAAK linkers. These rigid linkers offer a second option for expression of cargo proteins where a flexible linker is suboptimal due to, for example, aggregation or other issues.

Results are shown in FIG. 20.

Cargo Protein Activity Assay

Eut shells were isolated from E. coli C2566 cells harboring NHis-EutS and BTL2 (with or without the EutC[1-19] signal sequence) using the methods described above. The activity of the BTL2 cargo was measured using an in vitro assay. Reaction mix for the in vitro assay was prepared by adding 1 ml of para-nitro phenol-palmitate solution (30 mg PNP-palmitate in 10 ml isopraopanol) to 9 ml sonication buffer (50 mM Tris-HCl, 2 mM EDTA, pH 8). 2 µl of the isolated protein was added to 200 µl of the reaction mix, and incubated at 30° C., $OD_{420}$ of the samples was measured at different time-points. Assays of cell lysates were also performed, and served as controls. Protein concentrations were used for normalization.

Results are shown in FIG. 21.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference in their entirety. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

All headings are for the convenience of the reader and should not be used to limit the meaning of the text that follows the heading, unless so specified.

Sequence Listing Free Text

SEQ ID NO: 1
MDQKQIEEIVRSVMASMGQ

SEQ ID NO: 2
MQNELQTALFQAFDTLNLQ

What is claimed is:

1. A cell comprising:
   a non-native compartment comprising a proteinaceous shell, the proteinaceous shell comprising:
   at least one EutS polypeptide; and
   no more than three of EutM, EutN, EutL, and EutK.

2. The cell of claim 1 wherein the non-native compartment is self-assembled in vivo.

3. The cell of claim 1 wherein the non-native compartment further comprises at least one targeted enzyme.

4. The cell of claim 3 wherein the non-native compartment comprises a plurality of different targeted enzymes.

5. The cell of claim 3 wherein the at least one targeted enzyme comprises a compartment-specific targeting signal sequence.

6. The cell of claim 1 wherein the proteinaceous shell comprises a plurality of different BMC polypeptides.

7. The cell of claim 6 wherein the plurality of different BMC polypeptides comprises BMC polypeptides from different bacterial species.

8. The cell of claim 6 wherein the plurality of different BMC polypeptides comprises BMC polypeptides from different BMC operons.

9. The cell of claim 1 wherein at least one BMC polypeptide comprises an affinity tag.

10. A method of making a cell comprising a non-native compartment comprising:
    introducing into a host cell one or more polynucleotides that, collectively, encode EutS and no more than three of EutM, EutN, EutL, and EutK, thereby producing a transformed cell; and
    growing the transformed cell under conditions effective for the transformed cell to express the one or more polynucleotides and produce a non-native compartment comprising a proteinaceous shell comprising EutS polypeptide and no more than three of EutM, EutN, EutL, and EutK.

11. The method of claim 10 wherein the host cell comprises a bacterium.

12. The method of claim 11 wherein the bacterium comprises a member of the family Enterobacteriaceae.

13. The method of claim 12 wherein the member of the family Enterobacteriaceae comprises *E. coli*.

14. The method of claim 11 wherein the bacterium comprises a member of the family Shewanellaceae.

15. The method of claim 10 wherein the host cell comprises a yeast.

16. The method of claim 15 wherein the yeast comprises a member of the family Saccharomycetaceae.

17. The method of claim 16 wherein the member of the family Saccharomycetaceae comprises *Saccharomyces cerevisiae*.

18. The method of claim 10 wherein the host cell comprises an alga.

19. A method of making a cell comprising a non-native compartment comprising:
    providing a cell comprising a non-native compartment comprising:
    a proteinaceous shell comprising EutS but no more than three of EutM, EutN, EutL, and EutK, and
    at least one enzyme that catalyzes conversion of a substrate to a product; and
    growing the cell under conditions effective for the at least one enzyme to catalyze conversion of the substrate to a product.

20. The method of claim 19 wherein the product comprises a bioactive product.

21. The method of claim 19 wherein the product comprises a drug or a drug precursor.

22. The method of claim 19 wherein the product comprises a biofuel or a precursor of biofuel production.

23. The method of claim 19 wherein the at least one enzyme catalyzes a step in degrading or detoxifying a toxic substrate.

24. The method of claim 19 further comprising isolating at least a portion of the non-native compartments.

25. The method of claim 24 wherein at least a portion of the non-native compartment comprise an affinity tag and isolating at least a portion of the non-native compartments comprises contacting a sample comprising the non-native compartments with an affinity substrate having selective affinity for the affinity tag.

26. The cell of claim 1 comprising a plurality of compartments.

* * * * *

SEQUENCE LISTING

```
<160> NUMBER OF SEQ ID NOS: 2

<210> SEQ ID NO 1
<211> LENGTH: 19
<212> TYPE: PRT
<213> ORGANISM: S. enterica

<400> SEQUENCE: 1

Met Asp Gln Lys Gln Ile Glu Glu Ile Val Arg Ser Val Met Ala Ser
1               5                   10                  15

Met Gly Gln

<210> SEQ ID NO 2
<211> LENGTH: 19
<212> TYPE: PRT
<213> ORGANISM: S. enterica

<400> SEQUENCE: 2

Met Gln Asn Glu Leu Gln Thr Ala Leu Phe Gln Ala Phe Asp Thr Leu
1               5                   10                  15

Asn Leu Gln
```